(12) United States Patent
Yadegari et al.

(10) Patent No.: US 11,890,121 B2
(45) Date of Patent: Feb. 6, 2024

(54) APPARATUS FOR SHIELDING RADIATION

(71) Applicant: Armery Medical Technologies Inc., London (CA)

(72) Inventors: Andrew Barbod Yadegari, North York (CA); Andrew Stephen McLellan, London (CA); Stephen George McLellan, London (CA)

(73) Assignee: ARMERY MEDICAL TECHNOLOGIES INC., London (CA)

( * ) Notice: Subject to any disclaimer, the term of this patent is extended or adjusted under 35 U.S.C. 154(b) by 392 days.

(21) Appl. No.: 17/304,752

(22) Filed: Jun. 25, 2021

(65) Prior Publication Data
US 2021/0401383 A1 Dec. 30, 2021

Related U.S. Application Data

(60) Provisional application No. 62/705,391, filed on Jun. 25, 2020.

(51) Int. Cl.
*A61B 6/10* (2006.01)
*A61B 6/04* (2006.01)
*G21F 3/00* (2006.01)

(52) U.S. Cl.
CPC .............. *A61B 6/107* (2013.01); *A61B 6/0407* (2013.01); *G21F 3/00* (2013.01)

(58) Field of Classification Search
CPC ......... A61B 6/107; A61B 6/0407; G21F 3/00; A61G 13/124; A61G 2210/50; A61G 13/1235
See application file for complete search history.

(56) References Cited

U.S. PATENT DOCUMENTS 3,967,128 A * 6/1976 Smulewicz .......... A61B 6/0421
 5/601
3,984,696 A * 10/1976 Collica ................. A61B 6/107
 976/DIG. 335

(Continued)

FOREIGN PATENT DOCUMENTS

CA 2912174 A1 1/2015
CA 3006471 A1 11/2019
(Continued)

OTHER PUBLICATIONS

Extended European Search Report dated Nov. 23, 2021 in respect of European Application No. 21181695.4.

*Primary Examiner* — David A Vanore
(74) *Attorney, Agent, or Firm* — Bereskin & Parr LLP/S.E.N.C.R.L., s.r.l.

(57) ABSTRACT

An apparatus for shielding radiation emitted during a medical procedure. The apparatus includes a board positionable on top of a procedure table. The board extends laterally between a first board edge and a second board edge, and longitudinally between a third board edge and a fourth board edge. The board includes a plurality of apertures distributed along at least one of the board edges. At least one radiation shield is removably mountable to the board. The at least one radiation shield includes at least one peg engageable with any one of the apertures in the board. The apparatus can include a body shield assembly and/or an adjustable screen assembly.

20 Claims, 22 Drawing Sheets

(56) References Cited

U.S. PATENT DOCUMENTS

| | | | | |
|---|---|---|---|---|
| 4,893,323 A * | 1/1990 | Cook, III | ............ | A61B 6/0442 |
| | | | | 378/177 |
| 4,938,233 A * | 7/1990 | Orrison, Jr. | ......... | A61B 6/4423 |
| | | | | 128/853 |
| 5,006,718 A * | 4/1991 | Lenhart | ................. | G21F 3/00 |
| | | | | 250/519.1 |
| 6,325,538 B1 * | 12/2001 | Heesch | ............... | A61B 6/4452 |
| | | | | 250/517.1 |
| 6,481,888 B1 * | 11/2002 | Morgan | ................. | G21F 3/00 |
| | | | | 378/204 |
| 7,663,128 B2 * | 2/2010 | Arterson | ................ | G21F 3/03 |
| | | | | 250/519.1 |
| 8,569,725 B2 * | 10/2013 | Shimazu | ................. | G21F 3/00 |
| | | | | 250/515.1 |
| 8,586,955 B2 * | 11/2013 | Tay | ......................... | G21F 3/00 |
| | | | | 378/20 |
| 9,763,843 B2 | 9/2017 | Crisco et al. | | |
| 9,795,346 B2 * | 10/2017 | Wasson, Jr. | ............. | A61B 6/487 |
| 10,172,576 B2 * | 1/2019 | Shealy | ................ | A61B 6/4411 |
| 10,548,795 B2 * | 2/2020 | Conner | ............... | A61G 7/0513 |
| 10,932,976 B2 * | 3/2021 | Conner | ............. | A61G 13/1235 |
| 11,207,039 B2 * | 12/2021 | Foster | ..................... | G21F 3/00 |
| 11,219,566 B2 * | 1/2022 | Wilson | ................ | A61G 7/0503 |
| 2002/0148980 A1 * | 10/2002 | Cadwalader | ............ | G21F 1/103 |
| | | | | 250/515.1 |
| 2006/0191565 A1 * | 8/2006 | Nagae | .................. | H01G 9/2036 |
| | | | | 136/243 |
| 2006/0284123 A1 * | 12/2006 | Goldstein | .............. | A61B 6/107 |
| | | | | 250/515.1 |
| 2007/0029513 A1 * | 2/2007 | Treuth | ................... | A61B 6/107 |
| | | | | 250/519.1 |
| 2011/0184278 A1 * | 7/2011 | Goff | ........................ | A61B 6/04 |
| | | | | 128/877 |
| 2013/0175461 A1 * | 7/2013 | Lambert | .................. | G21F 3/00 |
| | | | | 250/517.1 |
| 2014/0316253 A1 | 10/2014 | Crisco et al. | | |
| 2016/0038365 A1 * | 2/2016 | Conner | ................ | A61B 6/0407 |
| | | | | 5/601 |
| 2016/0158082 A1 * | 6/2016 | Gainor | .................. | A61B 6/107 |
| | | | | 5/690 |
| 2016/0317110 A1 * | 11/2016 | Rees | ......................... | G21F 3/00 |
| 2017/0072223 A1 * | 3/2017 | Hsu | ........................... | G21F 3/00 |
| 2019/0029612 A1 * | 1/2019 | Bailey | .................... | A61B 6/035 |
| 2021/0401383 A1 * | 12/2021 | Yadegari | ............ | A61B 13/1235 |

FOREIGN PATENT DOCUMENTS

| | | |
|---|---|---|
| CN | 107661116 A | 2/2018 |
| DE | 202008006049 U1 | 8/2008 |
| DE | 202010012488 U1 | 11/2010 |
| WO | 2015/012906 A1 | 1/2015 |
| WO | 2017/218871 A1 | 12/2017 |
| WO | 2019/227210 A1 | 12/2019 |

* cited by examiner

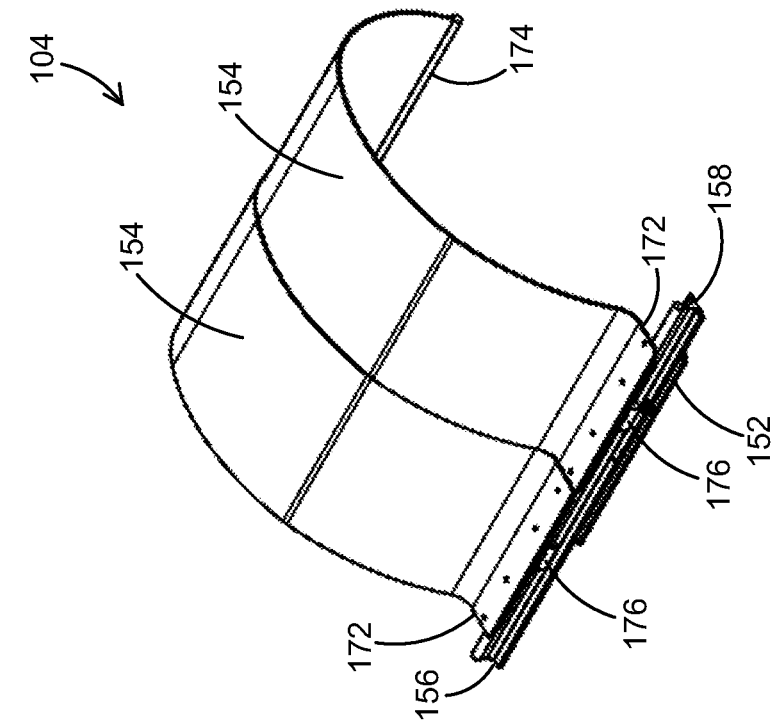
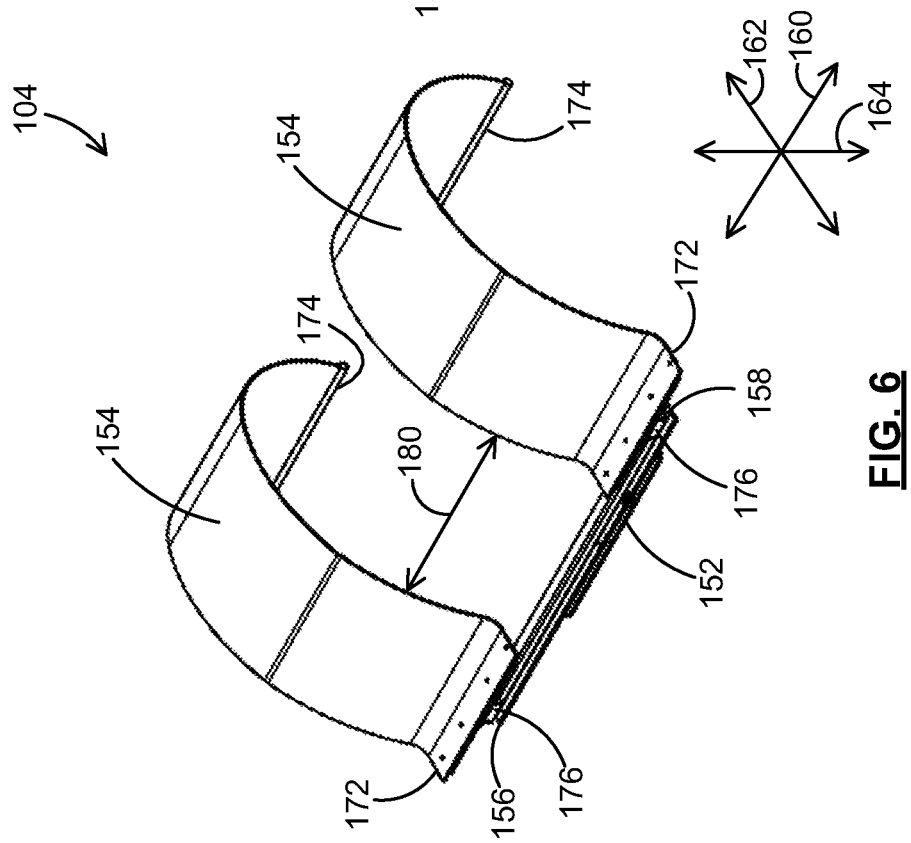

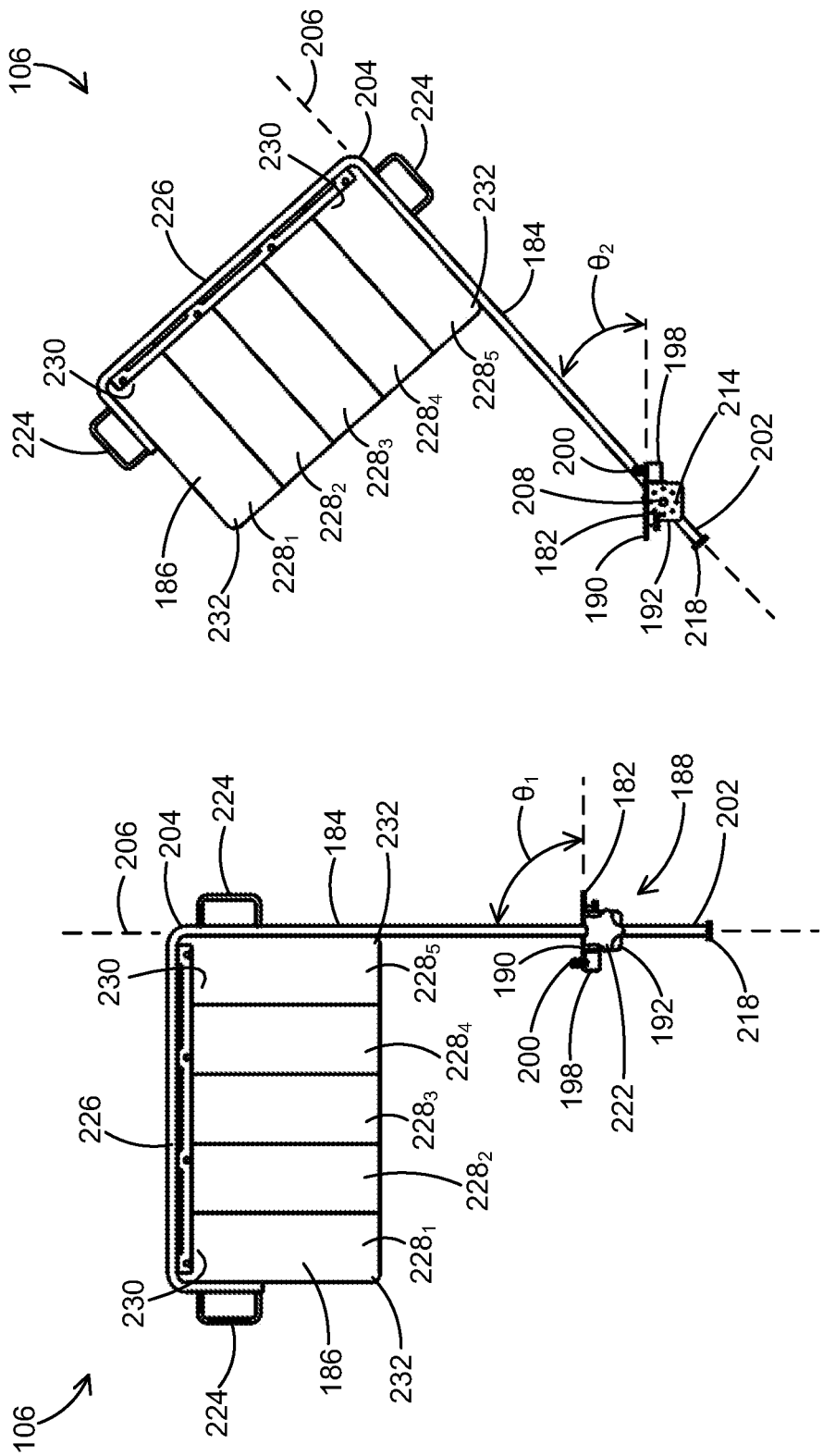

APPARATUS FOR SHIELDING RADIATION

CROSS-REFERENCE TO RELATED APPLICATION

This application claims priority to U.S. Provisional Application No. 62/705,391 filed on Jun. 25, 2020, the entire contents of which are hereby incorporated herein by reference.

FIELD

This present disclosure relates to an apparatus for shielding radiation during a medical procedure.

BACKGROUND

The following paragraphs are not an admission that anything discussed in them is prior art or part of the knowledge of persons skilled in the art.

United States Publication No. 2016/0038365 A1 describes systems and methods for left radial access, right room operation peripheral interventions that include left radial bases to stabilize a left arm of a cardiac patient across a midsagittal plane, transradiant right radial bases to position a right arm of the patient, and radiodense radiation reduction barriers located between the patient and a doctor.

U.S. Pat. No. 9,763,843 B2 describes a medical apparatus for use in supporting a patient lying in a supine position during a radial cardiac catheterization procedure. More particularly, an arm board is described for use with a patient's arm during a radial cardiac catheterization procedure. The arm board has a base member having a substantially planar support surface on which the patient's arm can be stabilized during a catheterization procedure and at least one shield member affixed to the base member and extending away from the support surface. The base member has both a radiolucent portion and a radiopaque portion and the shield member is a radiopaque material, thereby reducing and/or eliminating a doctor's exposure to radiation during radial cardiac catheterization procedures without impairing the ability to obtain the necessary medical images.

International Publication No. WO 2019/227210 A1 describes an apparatus for supporting an arm of a human patient during a medical procedure that can include a base, an arm pad, and barriers for shielding scatter radiation. A medial portion of the base can lie between the human patient and a table on which the human patient is supported. The arm pad can be positioned on a lateral portion of the base. A first barrier can be mounted to the base and can be positioned laterally intermediate the medial and lateral portions, the first barrier extending upwardly from the base to above the arm pad. A second barrier can be mounted to the lateral portion of the base and extend downwardly. The arm pad can include a radiopaque panel that is horizontal.

INTRODUCTION

The following summary is intended to introduce the reader to various aspects of the applicant's teaching, but not to define any invention.

In accordance with an aspect of the present disclosure, there is provided an apparatus for shielding radiation emitted during a medical procedure. The apparatus can include a board positionable on top of a procedure table, the board extending laterally between a first board edge and a second board edge, and longitudinally between a third board edge and a fourth board edge, the board including a plurality of apertures distributed along at least one of the board edges; and at least one radiation shield removably mountable to the board, the at least one radiation shield including at least one peg engageable with any one of the apertures in the board.

In accordance with another aspect of the present disclosure, there is provided an apparatus for shielding radiation emitted during a medical procedure. The apparatus can include: a board positionable on top of a procedure table, the board extending laterally between a first board edge and a second board edge; and a body shield assembly for shielding a patient supported above the procedure table from radiation, the body shield assembly can include: a longitudinally extending track removably mountable to the board along one of the first and second board edges; and at least one shield member extending from a first shield edge to a second shield edge, the first shield edge being attached to and slidable along the track.

In accordance with another aspect of the present disclosure, there is provided an apparatus for shielding radiation emitted during a medical procedure. The apparatus can include: a board positionable on top of a procedure table, the board extending laterally between a first board edge and a second board edge, and longitudinally between a third board edge and a fourth board edge; and an adjustable screen assembly for shielding radiation scatter above the procedure table, the adjustable screen assembly can include: a bracket including a mount and a ledge extending away from the mount, the mount being removably mountable to the board along one of the board edges; a clamping mechanism attached to the ledge; a shaft extending from a first shaft end to a second shaft end along a shaft axis; and a screen connected to the shaft proximate to the second shaft end, the clamping mechanism being configured to clamp the shaft to maintain a position of the screen above the board.

Other aspects and features of the teachings disclosed herein will become apparent, to those ordinarily skilled in the art, upon review of the following description of the specific examples of the present disclosure.

BRIEF DESCRIPTION OF THE DRAWINGS

The drawings included herewith are for illustrating various examples of apparatuses of the present disclosure and are not intended to limit the scope of what is taught in any way. In the drawings:

FIG. 6 is a perspective view of an example body shield assembly having first and second shield members shown in a spaced apart arrangement;

FIG. 7 is a perspective view of the body shield assembly of FIG. 6, with the first and second shield members shown in an adjoined arrangement;

FIG. 12 is a side view of the adjustable screen assembly of FIG. 11;

FIG. 13 is a side view of the adjustable screen assembly of FIG. 11, with the shaft shown in an angled position;

DETAILED DESCRIPTION

Figure 1:
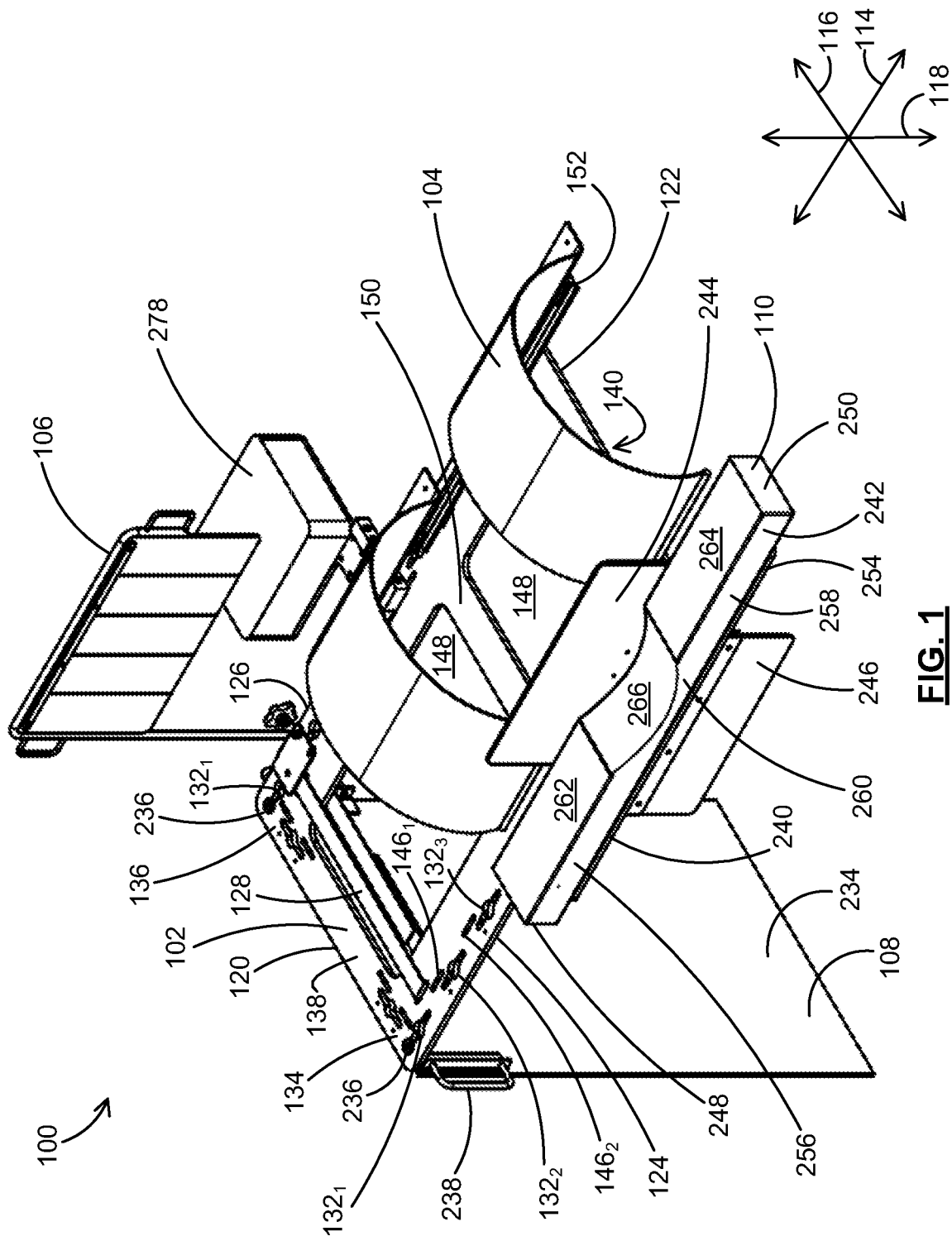
FIG. 1 is a perspective view of an example apparatus for shielding medical radiation.

Various apparatuses or methods will be described below to provide an example of an embodiment of each claimed invention. No embodiment described below limits any claimed invention and any claimed invention may cover apparatuses and methods that differ from those described below. The claimed inventions are not limited to apparatuses and methods having all of the features of any one apparatus or method described below, or to features common to multiple or all of the apparatuses or methods described below. It is possible that an apparatus or method described below is not an embodiment of any claimed invention. Any invention disclosed in an apparatus or method described below that is not claimed in this document may be the subject matter of another protective instrument, for example, a continuing patent application, and the applicant(s), inventor(s) and/or owner(s) do not intend to abandon, disclaim or dedicate to the public any such invention by its disclosure in this document.

It should be noted that terms of degree such as "substantially", "about" and "generally" as used herein mean a reasonable amount of deviation of the modified term such that the end result is not significantly changed. These terms of degree may also be construed as including a deviation of the modified term, such as by 1%, 2%, 5% or 10%, for example, if this deviation does not negate the meaning of the term it modifies.

As used herein and in the claims, a first element is said to be "received" in a second element where at least a portion of the first element is received in the second element unless specifically stated otherwise.

Some elements herein may be identified by a part number, which is composed of a base number followed by an alphabetical or subscript-numerical suffix (e.g. 136a, or $136_1$). Multiple elements herein may be identified by part numbers that share a base number in common and that differ by their suffixes (e.g. $136_1$, $136_2$, and $136_3$). All elements with a common base number may be referred to collectively or generically using the base number without a suffix (e.g. 136).

X-rays, gamma rays, and other forms of ionizing radiation are used to diagnose and treat many medical conditions. The emission of radiation during medical procedures can pose a significant health risk to both patients and healthcare professionals alike. Precautions are taken to limit not only the patient's exposure to radiation, but also the exposure to the staff members (e.g. doctors, nurses, and other healthcare professionals) that are present during these procedures. A staff member may perform thousands of medical procedures per year. Repeated exposure to radiation can pose a serious health risk.

The radiation to which staff members are most commonly exposed is radiation scatter. Radiation scatter is a type of secondary radiation that occurs when a beam intercepts an object, causing that beam to spread in different directions. Radiation scatter can be produced across a wide variety of different medical procedures, such as, for example, CT imaging, mammography, and pacemaker implantation. For many medical procedures, the patient's body is the object that deflects the radiation and causes it to scatter around the room. This means that anyone who is nearby may need to take precautions.

In some cases, staff members are able to step out of the room during the procedure (e.g. dental x-rays). In these cases, the likelihood of exposure to radiation scatter can be reduced. However, this may not be possible for many types of medical procedures (e.g. interventional cardiology, interventional radiology, vascular surgery, etc.). In these cases, one or more staff members may be required to be near the patient while the procedure is performed. Without appropriate protection, these staff members risk being exposed to unsafe levels of radiation. Regular exposure to scatter radiation adds up and may cause serious health issues over time. Scatter radiation is associated with skin damage, eye injury, and increased risk of cancerous lymphocytes and chromosomal abnormalities.

Current equipment, such as lead aprons and other shields, provide some protection to patients and to those staff members in attendance during the medical procedure. This equipment can be clumsy, unprofessional, and uncomfortable for the patient and can provide little or no additional radiation protection. It is desirable for patients and staff members to have their exposure to radiation further reduced. Staff members may perform thousands of medical procedures per year. This repeated exposure to radiation can pose a serious health concern over time if proper protection is not provided.

The present disclosure is directed at medical radiation shielding apparatuses that address the limited applications and other shortcomings of the equipment currently used for protection from medical radiation. In particular, the apparatuses disclosed herein can allow one or more radiation shields to be selectively positioned according to the type of medical procedure being performed, the size/orientation of the patient and/or the position of those performing the medical procedure. Thus, by allowing for such adaptability, the apparatuses disclosed herein may be used to provide radiation shielding for a number of different types of medical procedures that have different radiation shielding needs. This can reduce cost since radiation protection specific to each type of medical procedure may not need to be purchased.

In another aspect, the apparatuses disclosed herein may include one or more radiation shields that are easily and reliably adjusted or repositioned before and/or during the medical procedure. For example, the ability to adjust the position of a radiation shield during the medical procedure can allow an operator to gain access to a part of the patient's body that may otherwise have been inaccessible. Alternatively, or in addition, the ability to reposition a radiation shield during the medical procedure can allow an operator to get a better view of a part of the patient's body that may have otherwise been obscured from view.

Figure 2:
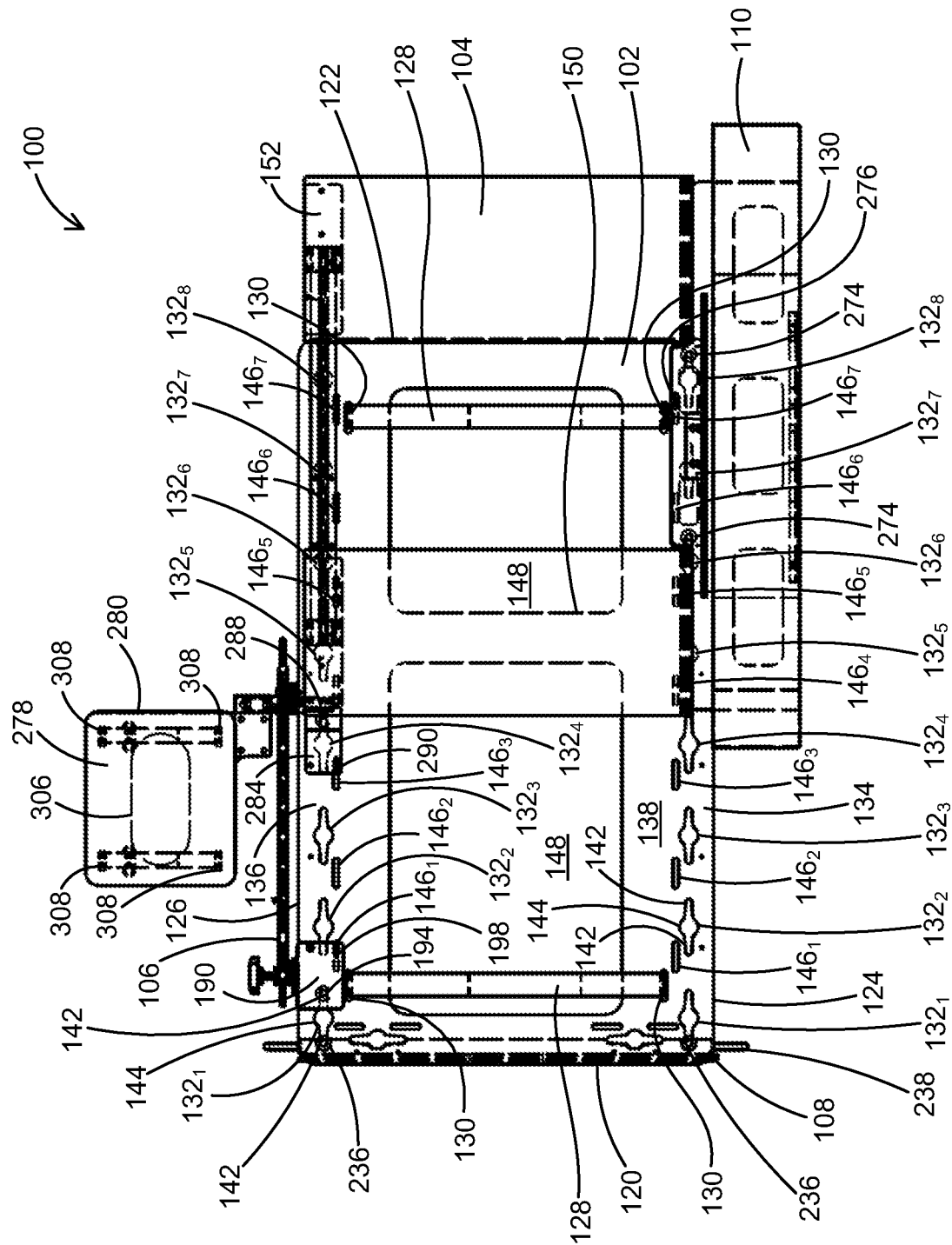
FIG. 2 is a top view of the apparatus of FIG. 1.
Figure 3:
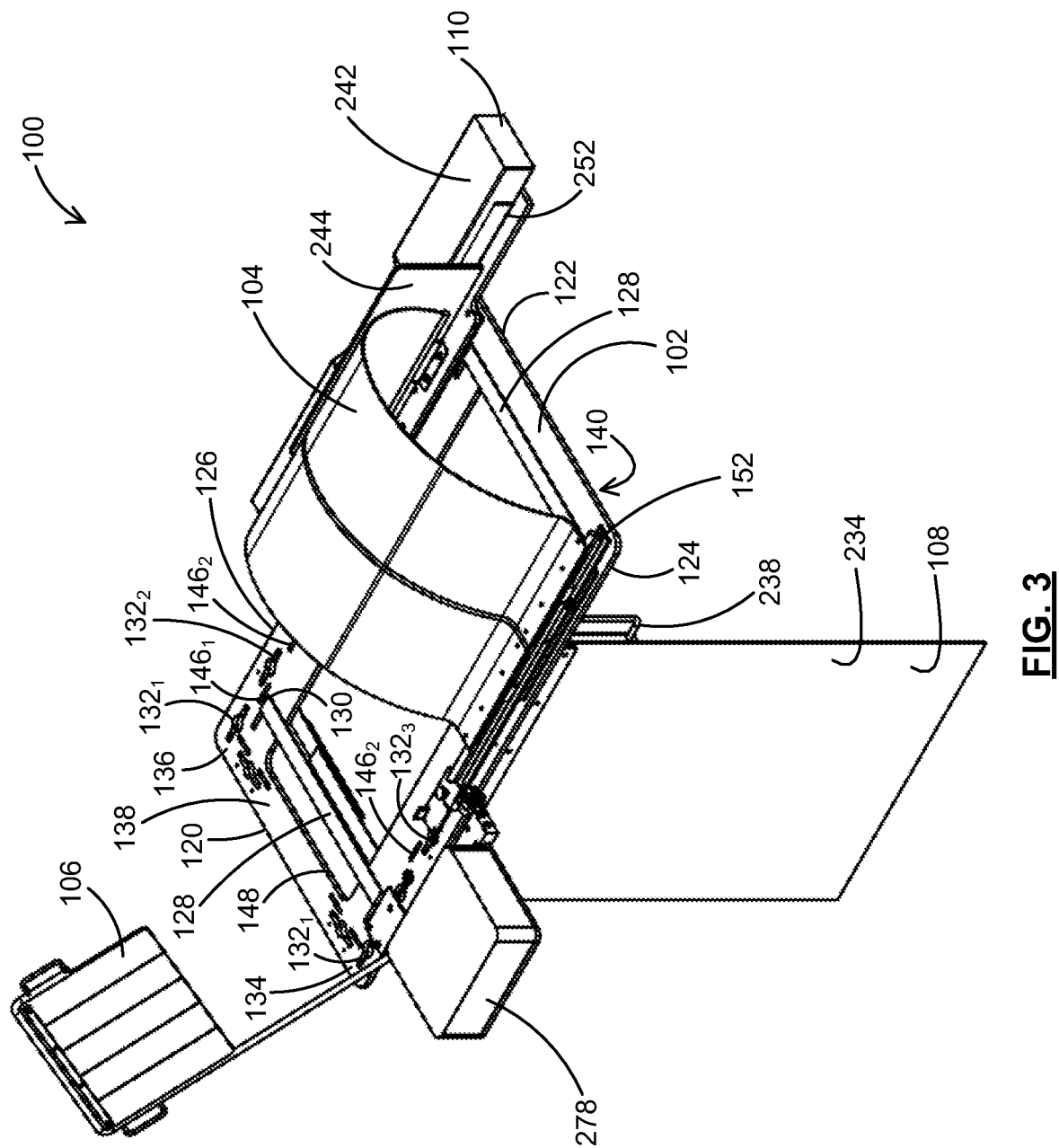
FIG. 3 is a perspective view of the apparatus of FIG. 1, with its various radiation shields in alternative positions.

FIGS. 1 to 3 illustrate an apparatus, referred to generally as 100, for shielding radiation emitted during a medical procedure. As shown, the apparatus 100 includes radiation shields 104, 106, 108, 110 that are respectively mounted to a board 102. The board 102 is shown to be generally planar and can be positioned on top of a procedure table (e.g. see procedure table 112 in FIGS. 20 and 21). In use, the board 102 lies between the procedure table and the patient. In some cases, the board 102 can be positioned under a mattress of the procedure table so that it does not make contact with the patient. As used herein, "procedure table" is meant to refer to any surface or platform that supports a patient above the floor during the medical procedure.

The board 102 extends in a longitudinal direction 114 between first and second board edges 120, 122, and in a lateral direction 116 between third and fourth board edges 124, 126. To aid with understanding, FIG. 1 includes a direction legend, in which the longitudinal direction 114, the lateral direction 116, and a vertical direction 118 are shown.

In use, one or more radiation shields are mounted to the board 102 to shield a patient and/or one or more attending staff members from radiation emitted during a medical procedure. Each radiation shield can be selectively positioned according to the type of medical procedure being performed, the size/orientation of the patient and/or the position of those in attendance. For example, comparing FIGS. 1 to 3 shows the radiation shields 104, 106, 108, 110 of the apparatus 100 in alternative positions.

As exemplified by radiation shields 104, 106, 108, 110 shown in FIGS. 1 to 3, radiation shields can be available in different configurations. The radiation shield 104 (also referred to herein as body shield assembly 104) can be mounted to the board 102 to shield a patient that is lying on the procedure table from radiation (e.g. see FIGS. 20 and 21). The radiation shield 106 (also referred to herein as adjustable screen assembly 106) can be mounted to the board 102 to shield an attending staff member from above table radiation scatter during the medical procedure. The radiation shield 108 (also referred to herein as skirt 108) can be mounted to the board 102 to shield one or more attending staff members from below table radiation scatter during the medical procedure. The radiation shield 110 (also referred to herein as shielded arm support 110) can be mounted to the board 102 to support one of the patient's arms and shield one of more attending staff members from radiation scatter during the medical procedure. Radiation shields 104, 106, 108, 110 are described in turn below.

The appropriate radiation shield(s) can be selected for use according to the specific shielding needs of the medical procedure. In some examples, the apparatus 100 includes multiple of any one or more (or all) of the radiation shields. For example, the apparatus 100 can include two of the skirts 108 to provide additional protection from below table radiation scatter. In some examples, the apparatus 100 does not include one or more of the radiation shields. For example, the apparatus 100 may not include the body shield assembly 104, and/or may not include the adjustable screen assembly 106, and/or may not include the skirt 108, and/or may not include the shielded arm support 110. Various configurations are possible.

In some cases, the board 102 is secured to the procedure table. This can limit or prevent unintended movement between the board 102 and the procedure table. The board 102 can be secured to the procedure table in a number of suitable manners. In the illustrated example, the board 102 is securable to the procedure table with a pair of belts 128. As perhaps best shown in FIG. 2, each belt 128 is fed through a pair of laterally spaced apart slits 130 formed in the board 102 and fastened by Velcro®. Alternatively, a clamp or another type of releasable fastener can be used instead of Velcro®. To secure the board 102 to the procedure table, each belt 128 can be tightened around the procedure table. This manner of securing the board 102 to the procedure table can allow for quick and easy installation by an end user (i.e. no need for professional installation). The board 102 can be removed from the procedure table when not in use, e.g. by loosening belts 128.

The board 102 includes a plurality of apertures 132 along at least one of the board edges 120, 122, 124, 126. As perhaps best shown in FIGS. 4 and 5, the board 102 as illustrated includes a plurality of apertures 132 located along each of the first, third and fourth board edges 120, 124, 126. The board 102 can have a board width in the lateral direction 116 (i.e. between the third and fourth board edges 124, 126) that is greater than the width of the procedure table. Accordingly, while positioned on top of the procedure table, the third and fourth board edges 124, 126 can project laterally beyond the edges of the procedure table to define corresponding board overhang regions 134, 136. Each of the apertures 132 located along the third and fourth board edges 124, 126 are located in one of the board overhang regions 134, 136. In some examples, the apertures 132 may be located along only one of the board edges 124, 126. In these examples, only the one of the third and fourth board edges 124, 126 on which the apertures 132 are located can project laterally beyond the procedure table while the board 102 is positioned on top of the procedure table.

Figure 4:
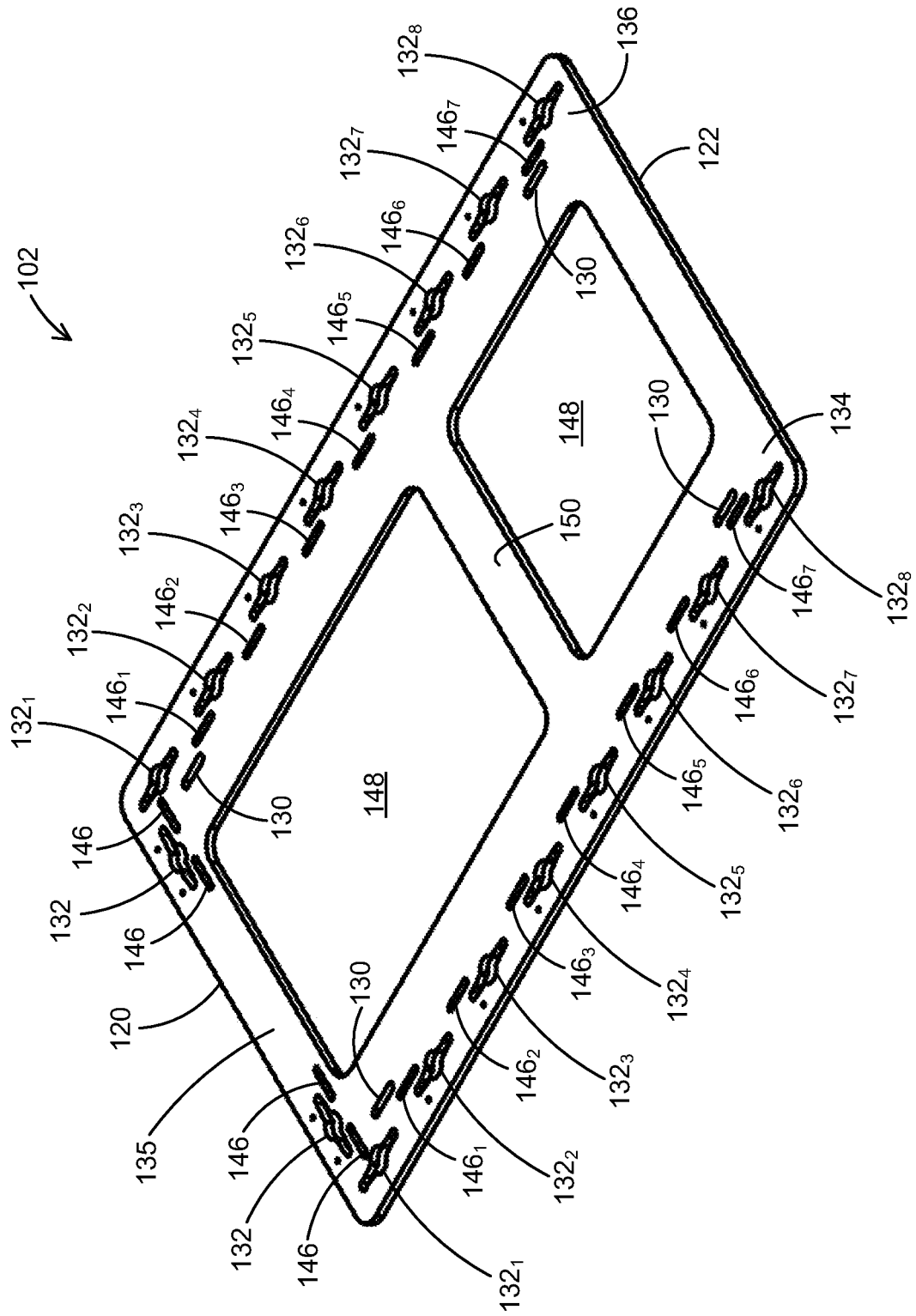
FIG. 4 is a perspective view of a board of the apparatus of FIG. 1.
Figure 5:
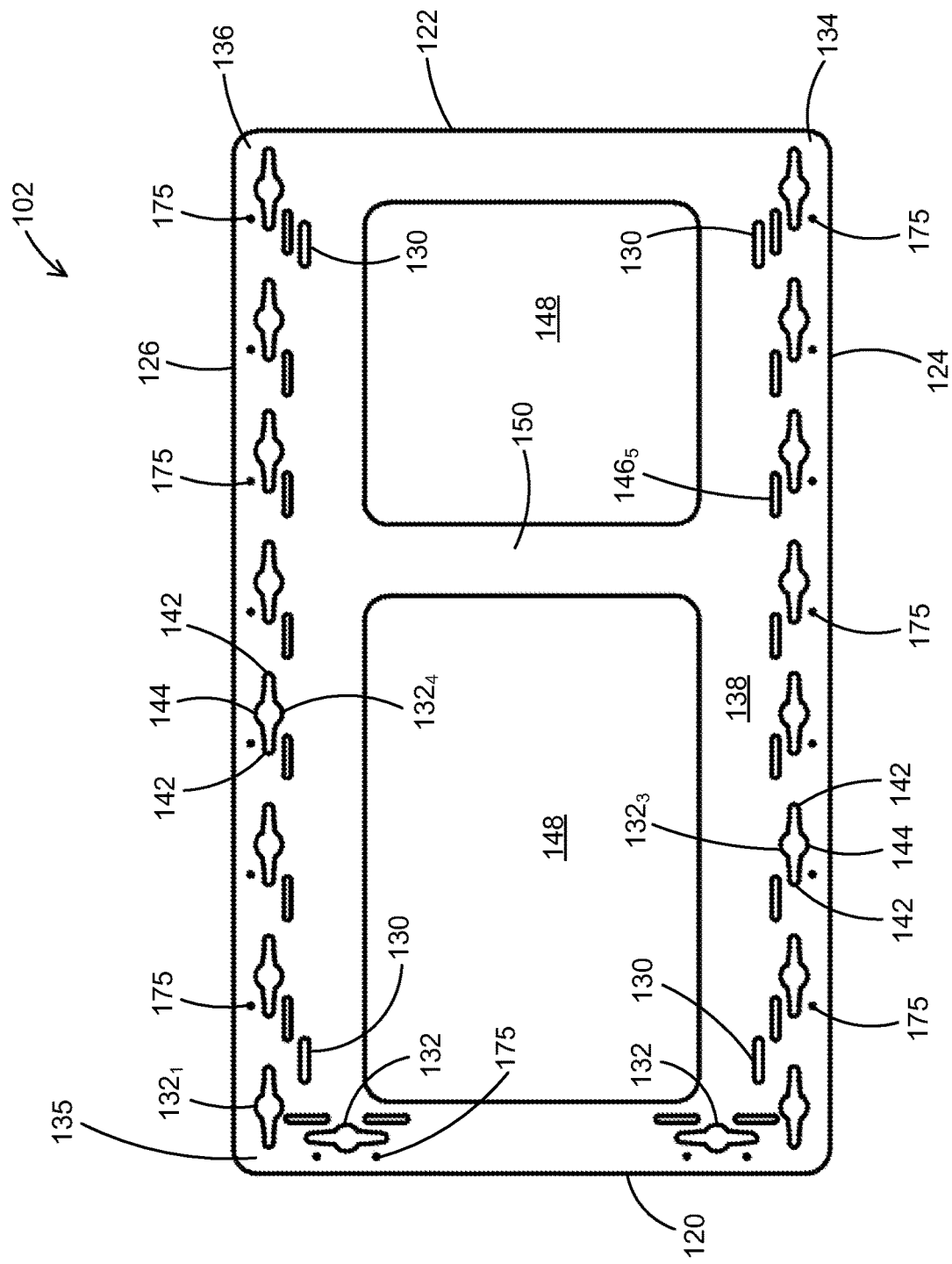
FIG. 5 is a top view of the board of FIG. 4.
Figure 8:
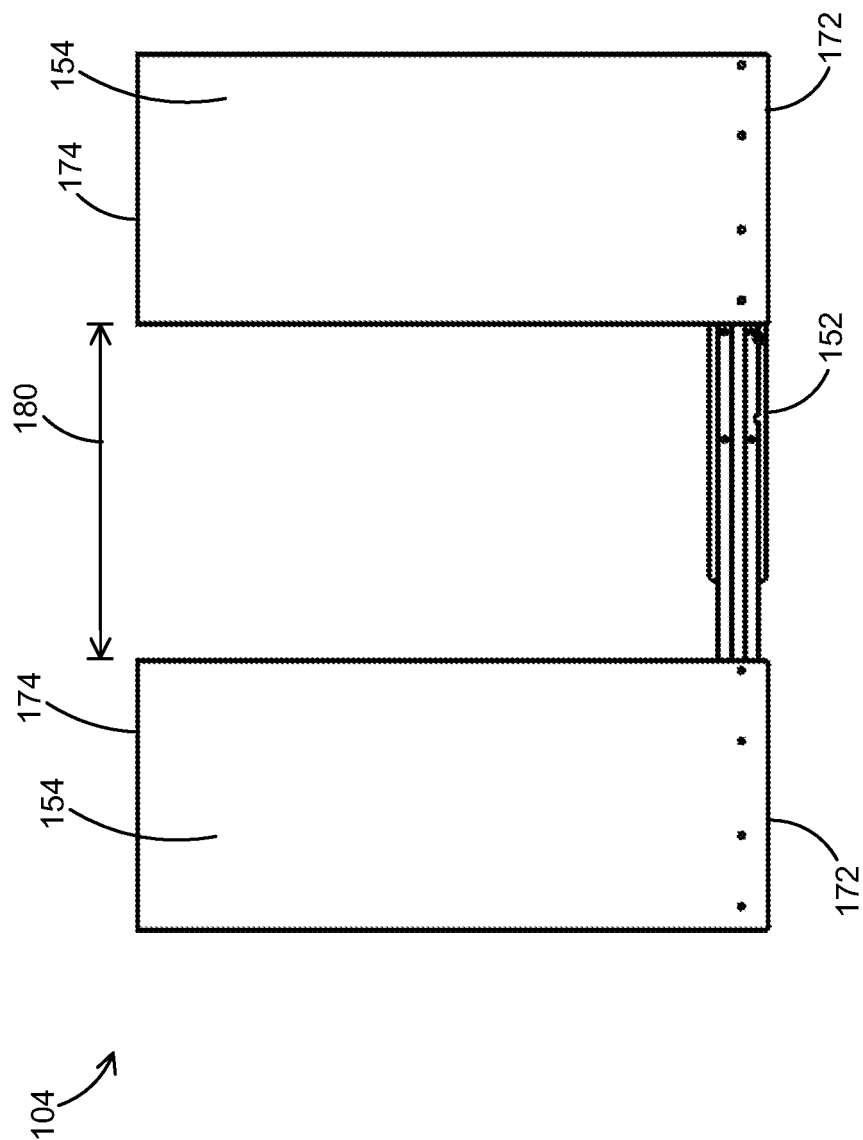
FIGS. 8, 9 and 10 are top, side and end views, respectively, of the body shield assembly of FIG. 6.

Referring still to FIGS. 4 and 5, the board 102 as illustrated includes two laterally spaced apart apertures 132 located along the first board edge 120. The board 102 can be positioned on the procedure table so that the first board edge 120 projects longitudinally beyond an edge of the procedure table to define a board overhang region 135. Each of the apertures 132 located along the first board edge 120 can be located in the board overhang region 135. As will be described below, the apertures 132 located along the first board edge 120 can provide a greater number of potential mounting positions for the radiation shields (e.g. radiation shield 106). In one or more alternative examples, more or less apertures 132 may be provided along the first board edge 120. As an example, four apertures 132 may be located along the first board edge 120. As another example, six apertures 132 may be located along the first board edge 120. Each radiation shield has at least one peg (e.g. see pegs 166 of radiation shield 104 in FIG. 9). Each peg can be engaged with any one of the apertures 132 to mount the radiation shield to the board 102. As best shown in FIGS. 1 and 3, the board 102 has opposed first and second board sides 138, 140. The first and second board sides 138, 140 extend in the longitudinal direction 114 between the first and second board edges 120, 122, and in the lateral direction 116 between the third and fourth board edges 124, 126. The pegs of each radiation shield (e.g. the radiation shields 104, 106, 108, 110) can be engaged with any one of the apertures 132 in the board 102 from either the first board side 138 or the opposed second board side 140. Accordingly, while the board 102 is positioned on top of the procedure table, each radiation shield can be mounted to the board 102 from above or below. For example, as perhaps best shown in FIG. 1, the adjustable screen assembly 106 is mounted to the board 102 from above while the skirt 108 is mounted to the board 102 from below. The ability to mount each radiation shield to the board 102 from either above or below can be advantageous in cases where mounting a radiation shield to the board 102 is obstructed from one of the first and second board sides 138, 140 (e.g. by another radiation shield).

In the illustrated example, eight apertures $132_{1-8}$ are evenly distributed along each of the third and fourth board edges 124, 126. The apertures $132_1$ are located proximate to the first board edge 120, and the apertures $132_8$ are located proximate to the second board edge 122. Accordingly, the apertures $132_{1-8}$ as illustrated are distributed along almost the entire length of the third and fourth board edges 124, 126 (i.e. end-to-end). Such a widespread distribution of apertures 132 can provide for a greater range in potential mounting locations for radiation shields (e.g. radiation shields 104, 106, 108, 110). In one or more alternative examples, the apertures 132 may be unevenly distributed along one or each of the third and fourth board edges 124, 126. Alternatively, or in addition, the apertures 132 may be distributed along only a portion (e.g. 50% or 75%) the length of the third and fourth board edges 124, 126.

As exemplified by comparison of FIGS. 1 to 3, the distribution of apertures $132_{1-8}$ along each of the third and fourth board edges 124, 126 allows for the mounting of the radiation shields 104, 106, 108, 110 at multiple locations (e.g. according to the needs of the medical procedure). The distance between adjacent apertures 132 can provide valuable versatility in the positioning of the radiation shields.

In one or more alternative examples, more or less apertures 132 may be provided along one or each of the third and fourth board edges 124, 126. As an example, ten apertures 132 may be located along each of the third and fourth board edges 124, 126. As another example, two apertures 132 may be located along the third board edge 124 and five apertures 132 may be located along the fourth board edge 126. In general, the greater the number of apertures 132 along each of the third and fourth board edges 124, 126, the greater the number of potential mounting locations for each radiation shield. However, when the apertures 132 are located too close to each other, the strength of the board material between adjacent apertures 132 can be compromised (i.e. weakened). In selecting an appropriate number of apertures 132 to provide along each of the third and fourth board edges 124, 126, a balance can be struck between versatility and durability.

In the illustrated example, each one of the apertures 132 distributed along the third board edge 124 is longitudinally aligned with a corresponding one of the apertures 132 distributed along the opposite fourth board edge 126. This alignment may provide for one or more advantages. For example, it may provide uniformity in mounting locations for the radiation shields between each of the third and fourth board edges 124, 126. Alternatively, or in addition, it may allow the board 102 to be inverted without significant change in the location of the apertures 132.

As perhaps best shown in FIG. 5, each aperture 132 in the board 102 includes an opposed pair of retention regions 142 extending away from an insertion region 144. In the illustrated example, the retention regions 142 of the apertures 132 located along each of the third and fourth board edges 124, 126 extend in the longitudinal direction 114 from the insertion region 144. In the illustrated example, the retention regions 142 of the apertures 132 located along the first board edge 120 extend in the lateral direction 116 from the insertion region 144. In one or more alternative examples, the retention regions 142 of any one of the apertures 132 may extend an angle to the longitudinal direction 114 from the insertion region 144.

As previously described, each radiation shield has at least one peg that can be engaged with any one of the apertures 132 in the board 102. The pegs are configured to be received in the insertion region 144 of any one of the apertures 132 and slidably engaged with one of the retention regions 142 of that aperture. For example, referring to FIG. 14, the peg 194 of radiation shield 106 can be inserted into the insertion region 144 of any one of the apertures 132 in the board 102 and then slid toward one of the two retention regions 142 of that aperture. The reduced size of the retention regions 142 compared to the insertion region 144 can prevent the peg 194 from disengaging the aperture 132 (unless slid back to the insertion region 144). The peg 194 has a head 196 that is smaller than the insertion region 144 yet larger than the retention regions 142. Accordingly, once the peg 194 has been slid from the insertion region 144 to one of the retention regions 142, the size of the head 196 can impede disengagement of the peg 194 from that retention region 142.

The ability to mate each peg of a radiation shield in either retention region 142 can allow the same aperture 132 to be engaged by the pegs of two different radiation shields at the same time. This can be particularly advantageous in cases where it is desirable to have two radiation shields mounted to the board 102 in the same region. For example, as shown in FIG. 2, the aperture $132_1$ at the fourth board edge 126 is engaged with pegs of both the radiation shield 106 and the radiation shield 108 (i.e. one retention region 142 is engaged with a peg 194 of the adjustable screen assembly 106 while the other retention region 142 is engaged with a peg 236 of the skirt 108). As exemplified in FIG. 2, the presence of the opposed pair of retention regions 142 allows for an above table radiation shield (e.g. the adjustable screen assembly 106) and a below table radiation shield (e.g. the skirt 108) to be engaged with the same aperture 132 at the same time.

The board 102 can include a plurality of alignment slots 146 located along at least one of the board edges 120, 122, 124, 126. As will be described below, the location of the alignment slots 146 can correspond to the location of the apertures 132 in the board 102. As perhaps best shown in FIGS. 4 and 5, the board 102 includes a plurality of alignment slots 146 located along each of the first, third and fourth board edges 120, 124, 126. In the illustrated example, the alignment slots 146 are located inboard of the apertures 132. In an alternative example, the alignment slots 146 can be located outboard of the apertures 132.

In the illustrated example, seven alignment slots $146_{1-7}$ are evenly distributed along each of the third and fourth board edges 124, 126. In the illustrated example, two alignment slots 146 are positioned adjacent to each of the two apertures 132 located at the first board edge 120 (i.e. four alignment slots 146 in total). In one or more alternative examples, more or less alignment slots 146 may be distributed along one or each of the first, third and fourth board edges 120, 124, 126.

As with the apertures 132, each alignment slot 146 is located in one of the board overhang regions 134, 135 and 136 that are defined while the board 102 is positioned on the procedure table. In some examples, the apertures 132 may be located along only one or two of the first, third and fourth board edges 120, 124, 126. In these examples, only the edges 120, 124, 126 on which the apertures 132 are located need to include alignment slots 146.

Figure 9:
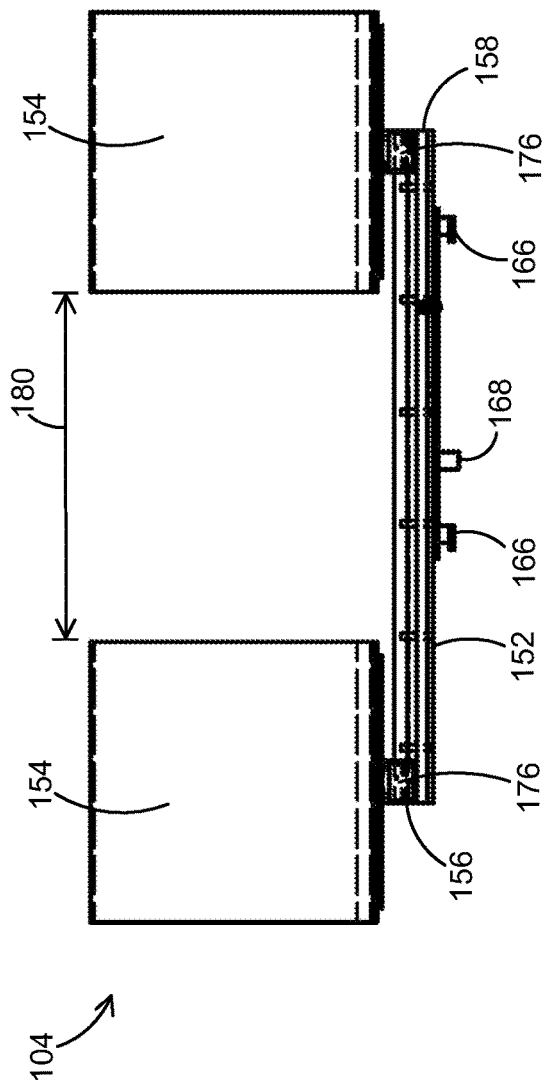

Each radiation shield can have an alignment flange (e.g. see alignment flange 168 of radiation shield 104 in FIG. 9). The alignment flange can be received in one of the alignment slots 146 in the board 102. Which alignment slot 146 receives the alignment flange of the radiation shield depends on which of the apertures 132 receive its peg(s). To ensure fit, the arrangement of the pegs(s) and the alignment flange of each radiation shield can correspond to the arrangement of the apertures 132 and the alignment slots 146 in the board 102. For example, referring to FIG. 14, the radiation shield 106 has a peg 194 and an alignment flange 198 that are specifically arranged to correspond with the location of apertures 132 and alignment slots 146 in the board 102 (FIG. 5).

Engagement between an alignment flange of a radiation shield and an alignment slot 146 in the board 102 can provide one or more advantages. For example, when mounting the radiation shield to the board 102, this engagement can help align the peg(s) with the apertures 132 in the board 102 by limiting relative rotation between the radiation shield and the board 102. Alternatively, or in addition, engagement between an alignment flange of a radiation shield and an alignment slot 146 can improve the stability of the connection between that radiation shield and the board 102.

Engagement between an alignment flange of a radiation shield and an alignment slot 146 in the board 102 can also facilitate mounting and/or removal of that radiation shield from the board 102. The alignment flange of each radiation shield is smaller than the alignment slots 146 in the board 102. Accordingly, once an alignment flange is received in one of the alignment slots 146, it can slide (i.e. side-to-side) within that alignment slot 146. In the illustrated example, the alignment slots 146 are positioned relative to the apertures 132 so that they restrict the peg(s) of the radiation shield to sliding between (i) the insertion region 144 of an aperture 132 and (ii) one of the two retention regions 142 of that aperture 132. While removing the radiation shield, contact between the alignment flange and alignment slot 146 can prevent the peg(s) from sliding past the insertion region 144 and into the other retention region 144.

The board 102 may be formed of a number of suitable materials, e.g. plastics, metals, carbon fiber, etc. In some examples, the board 102 is formed of a unitary piece of polycarbonate material. Polycarbonates are strong and durable materials that are easily worked, molded and thermoformed. In addition, polycarbonates can be more radiolucent than other materials, which can reduce the amount of radiation needed during medical imaging.

With reference to FIG. 1, the board 102 can have a board length in the longitudinal direction 114 between about 50 cm and about 225 cm, or between about 80 and about 160 cm. The board 102 can have a board width in the lateral direction 116 between about 50 cm and about 100 cm, or between about 60 cm and about 80 cm. The board 102 can have a board thickness in the vertical direction 118 between about 0.1 cm and about 5 cm, or between about 0.2 cm and about 2 cm. These dimensions are intended to be illustrative but non-limiting. Various configurations are possible.

As perhaps best shown in FIGS. 4 and 5, the board 102 includes a pair of void regions 148. The void regions 148 can be cutouts of the board 102. Alternatively, the board 102 may be formed with the void regions 148. In the illustrated example, the void regions 148 are separated by a linking segment 150 that acts to maintain the structural integrity of the board 102. The void regions 148 in the board 102 can provide several advantages. For example, the void regions 148 may decrease impedance during medical imaging and thereby avoid degradation of medical image quality. The void regions 148 can reduce the amount of board material in the path of the x-ray beam. Alternatively, or in addition, the void regions 148 may reduce the weight of the board 102, thereby making it easier to install and/or move around.

Reference is now made to FIGS. 6 to 10, which illustrate a body shield assembly, referred to generally as 104, for shielding a patient supported above the procedure table from radiation. As shown, the body shield assembly 104 includes a track 152 and a pair of movable shield members 154. In alternative examples, the body shield assembly 104 may include a greater (e.g. 3-5) or a smaller (e.g. one) number of shield members 154.

The track 152 extends in a longitudinal direction 160 between first and second track ends 156, 158. The track 152 can be mounted to the board 102 along one of the third and fourth board edges 124, 126 (e.g. see FIGS. 1 and 3). To aid with understanding, FIG. 6 includes a direction legend, in which the longitudinal direction 160, a lateral direction 162, and a vertical direction 164 are shown.

The body shield assembly 104 can be mounted to the board 102 either before or after the patient is positioned on the procedure table. The track 152 includes at least one peg that can engage with any one of the apertures 132 to mount the body shield assembly 104 to the board 102. Referring to FIG. 9, the track 152 as illustrated includes a pair of spaced apart pegs 166. The stability of the connection between the track 152 and the board 102 can be improved by spacing the pegs 166 apart, e.g. as shown. To ensure fit, the distance between the pegs 166 of the track 152 can correspond to the distance between multiple pairs of the apertures 132 in the board 102. For example, if the distance between the pegs 166 is 20 cm, the board 102 can have a plurality of aperture pairs that are similarly spaced apart by 20 cm. In the illustrated example, the track 152 can be mounted at multiple locations along either of the third and fourth board edges 124, 126. For example, FIG. 2 shows the track 152 mounted along the fourth board edge 126 with the pegs 166 correspondingly engaged with the apertures $132_6$ and $132_8$.

Referring again to FIG. 9, the pegs 166 as illustrated extend downwardly and perpendicularly from the track 152. The pegs 166 are configured to be received in the insertion region 144 of corresponding apertures 132 and slidably engaged with one of the retention regions 142 of those apertures. As previously described, the reduced size of the retention regions 142 compared to the insertion region 144 can prevent the pegs 166 from disengaging the apertures 132 (unless slid back to the insertion regions 144).

Before the medical procedure, the patient can be transferred onto the procedure table (e.g. from a stretcher). The side from which the patient is transferred onto the procedure table can be fixed and/or dependent on room setup.

The ability to mount the track 152 along either one of the third and fourth board edges 124, 126 allows it to be mounted on the board edge opposite to the side of the procedure table used for patient transfer (i.e. thereby getting it out of the way).

Referring still to FIG. 9, the track 152 as illustrated includes an alignment flange 168 located between the pegs 166. The alignment flange 168 extends downwardly and perpendicularly from the track 152. While mounting the track 152 to the board 102, the alignment flange 168 is received in a corresponding alignment slot 146. Which alignment slot 146 receives the alignment flange 168 of the track 152 depends on which of the apertures 132 in the board 102 receive the pegs 166. To ensure fit, the arrangement of the pegs 166 and the alignment flange 168 of the track 152 correspond to the arrangement of the apertures 132 and the alignment slots 146 in the board 102. This can allow the track 152 to be mounted at multiple locations along either of the third and fourth board edges 124, 126. For example, FIG. 2 shows the track 152 mounted at the board edge 126 with its alignment flange 168 received in the alignment slot $146_7$. The pegs 166 and alignment flange 168 can cooperate to simplify installation and/or improve the stability of the connection between the track 152 and the board 102. In some examples, the track 152 may not include an alignment flange 168.

Figure 10:
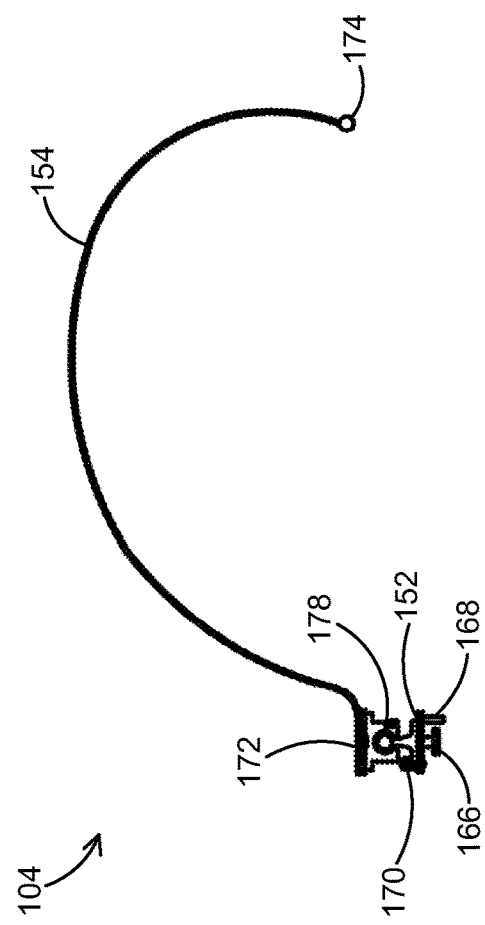

Referring to FIG. 10, the track 152 as illustrated includes a compression screw 170. Once the track 152 is mounted to the board 102, e.g. as described above, the compression screw 170 can be tightened into the board 102. As perhaps best shown in FIGS. 4 and 5, the board 102 as illustrated includes a plurality of threaded openings 175 to receive the compression screw 170. Each of the threaded openings 175 in the board 102 are located relative to the apertures 132 and alignment slots 146 so that is position aligns with the position of the compression screw 170 of the track 152. In this way, the compression screw 170 may be used to limit relative movement between the track 152 and the board 102, thereby stabilizing the connection between the body shield assembly 104 and the board 102. Tightening compression screw 170 into the board 102 can also limit unintentional dismounting of the track 152 from the board 102. The compression screw 170 can be loosened prior to dismounting the track 152 from the board 102. In some examples, the track 152 may not include a compression screw 170.

Referring again to FIGS. 6 and 7, each shield member 154 extends in the lateral direction 162 between first and second shield edges 172, 174. The first shield edge 172 is attached to and slidable along the track 152. The shield member 154 can be slidably attached to the track 152 in a number of suitable manners. In the illustrated example, a slider 176 attaches the first shield edge 172 to the track 152. As shown in FIG. 10, the slider 176 has a longitudinally extending groove 178 that receives the track 152.

With reference to FIGS. 6 and 7, the shield members 154 are independently slidable along the track 152 between an adjoined arrangement and a spaced apart arrangement. FIG. 7 shows the shield members 154 in the adjoined arrangement. In the adjoined arrangement, the shield members 154 abut each other. Accordingly, in the adjoined arrangement, the shield members 154 collectively form one larger shield. In some examples, the shield members 154 can be partially overlapped to avoid any gap being defined between them.

FIG. 6 shows the shield members 154 in the spaced apart arrangement. In the spaced apart arrangement, the shield members 154 define a longitudinal gap 180 therebetween. The gap 180 can be adjusted by sliding one or each of the shield members 154 along the track 152. The track 152 has a track length in the longitudinal direction 160 (i.e. between the first and second track ends 156, 158). In FIG. 6, the gap 180 defined between the shield members 154 is maximized for the given track length. In some examples, the gap 180 is adjustable between about 0 cm and about 100 cm.

All else being equal, the longer the track length, the larger the gap 180 that can be defined between the shield members 154. The track length can be between about 20 cm and about 150 cm, or between about 50 cm and about 100 cm. These dimensions are intended to be illustrative but non-limiting. In some examples, the shield members 154 can be prevented from disengaging (i.e. sliding off) the track 152 at each of the first and second tracks ends 156, 158. For example, an endcap (not shown) can be mounted at the first and second tracks ends 156, 158 to prevent disengagement of the shield members 154 due to over sliding.

Figure 21:
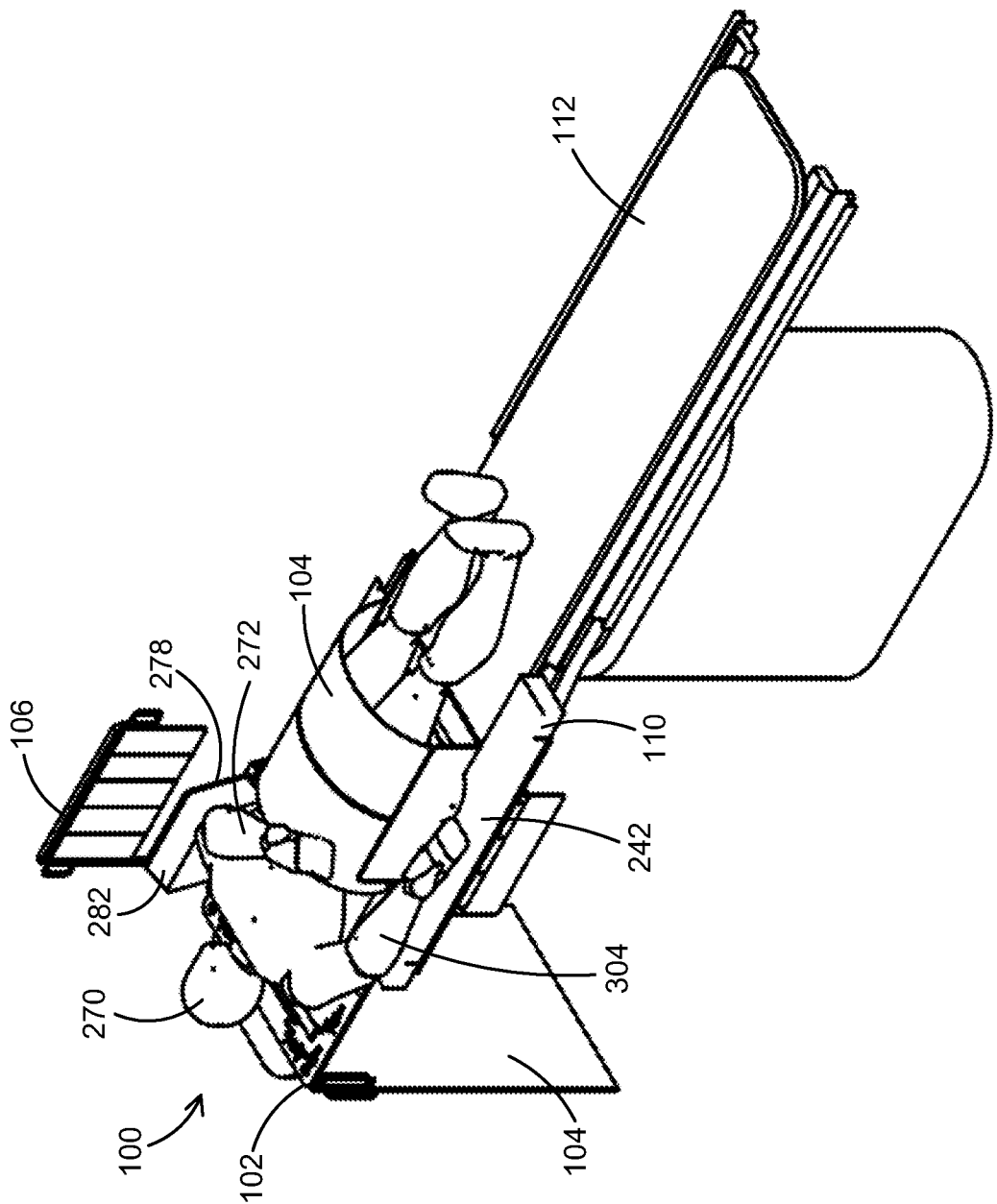

One can position the shield members 154 between the adjoined and the spaced apart arrangements according to the needs of the medical procedure and/or the patient's size/height. For example, the shield members 154 can be positioned in the adjoined arrangement to cover the patient's pelvis and abdomen while performing a transradial cardiac catheterization. Alternatively, the shield members 154 can be positioned in the spaced apart arrangement to cover a patient's chest and pelvis while leaving a gap to access the abdomen. For example, referring to FIG. 21 shows the shield members 154 covering the abdomen and upper legs of a patient 270 that is lying on a procedure table 112.

Furthermore, some medical procedures require unplanned access to areas of the patient's body that are initially covered by the shield members 154. In these cases, those in attendance can adjust the position of one or each of the shield members 154 during the medical procedure to expose an area of interest, e.g. a patient's groin for femoral arterial access. The ability to quickly reposition the shield members 154 by sliding them along the track 152 can allow for dynamic adjustments while maintaining a high level of protection from radiation and sterility.

The shield members 154 have a shield width in the lateral direction 162 (i.e. between the first and second shield edges 172, 174). The shield width can be between about 50 cm and about 150 cm, or between about 70 cm and about 100 cm. These dimensions are intended to be illustrative but non-limiting. In use, the shield members 154 extend around the patient's body (i.e. from side-to-side) to impede passage of radiation. In cases where the shield members 154 do not extend all the way around the patient's body, the exposed area can be unprotected. Given the variability of patient sizes, a shield width can be selected to be sufficient to extend around the torsos of large patients.

As best shown in FIG. 10, the shield members 154 are flexible along the entire shield width. This flexibility can allow the shield members 154 to take the shape of the patient's body (e.g. torso or legs depending on position). In FIGS. 6 to 10, the shield members 154 are shown how they would look while draped over a patient's torso. When not in use, the shield members 154 can lie flat.

With reference to FIGS. 6 and 7, the shield members 154 have a shield length in the longitudinal direction 160. The shield length can be between about 5 cm and about 60 cm, or between about 20 cm and about 50 cm. These dimensions are intended to be illustrative but non-limiting. In the illustrated example, the shield members 154 have the same shield length. In one or more alternative examples, the shield members 154 may have different shield lengths. For example, one shield member 154 may have a shield length twice that of the other shield member 154. Various configurations are possible.

The shield members 154 can be formed at least partially of substantially radiopaque material, e.g. for example, lead, tin, antimony, tungsten or bismuth. In some examples, the shield members 154 are formed of vinyl coated lead rubber. The vinyl coating can improve safety by preventing direct contact with lead.

In some examples, the second shield edge 174 can be magnetically secured to the board 102 at one of the third and fourth board edges 124, 126. For example, the shield members 154 can include one or more shield magnets (not shown) disposed along the second shield end 174. The one or more shield magnets can collectively produce a magnetic field. The board 102 can include one or more board magnets (not shown) disposed along one or each of the third and fourth board edges 124, 126. The one or more board magnets can collectively produce a magnetic field. In close proximity, interaction between the magnetic fields produced by the shield and board magnets can magnetically attract the second shield edge 174 to the board 102. A magnet's orientation may be described by reference to its North (N) and South (S) magnetic poles. When matching poles (i.e. N-N or S-S) of two magnets are brought into proximity to each other, the magnetic fields of those magnets produce an attraction force that urges the magnets to come together (as opposed to a repulsion force that urges the magnet to separate). Magnetically securing the second shield edge 174 to the board 102 can prevent the shield member 154 from slipping off the patient once it has been appropriately positioned. This may be particularly important in cases where the shield members 154 are covered with a sterile bag that makes them more slippery.

Reference is now made to FIGS. 11 to 14, which illustrate an adjustable screen assembly, referred to generally as 106, for shielding radiation scatter above the procedure table. As shown, the adjustable screen assembly 106 includes a bracket 182, a shaft 184, a screen 186 and a clamping mechanism, referred to generally as 188. The bracket 182 has a mount 190 and a ledge 192 that extends away from the mount 190. In the illustrated example, the ledge 192 extends generally downwardly and perpendicularly from mount 190, thereby giving the bracket 182 an L-shape appearance.

Figure 14:
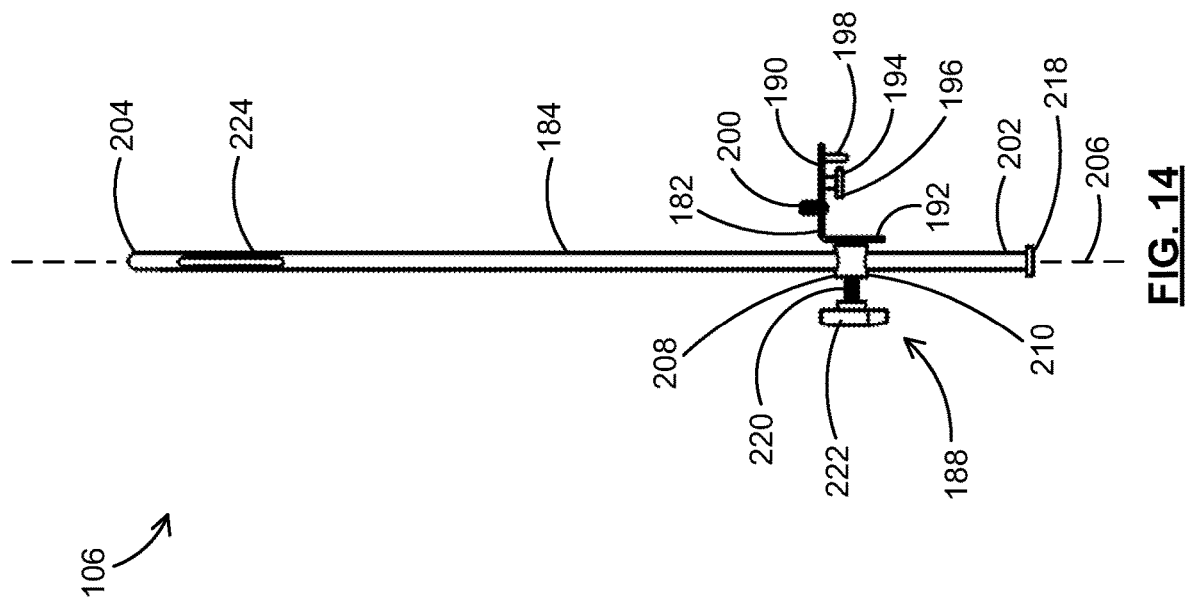
FIG. 14 is an end view of the adjustable screen assembly of FIG. 11.
Figure 15:
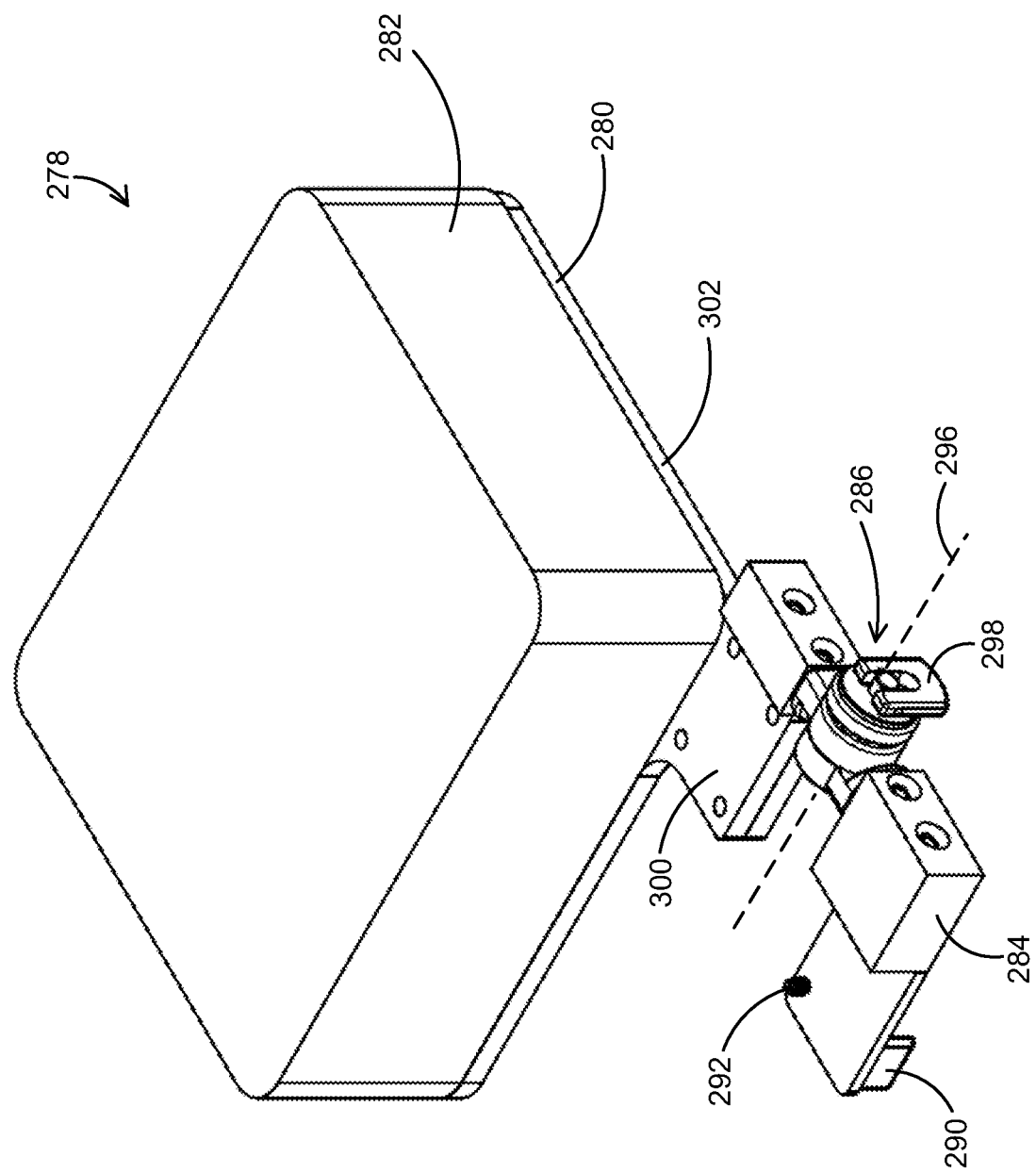
FIG. 15 is a perspective view of an example pivotable arm support, shown in a horizontal position.
Figure 16:
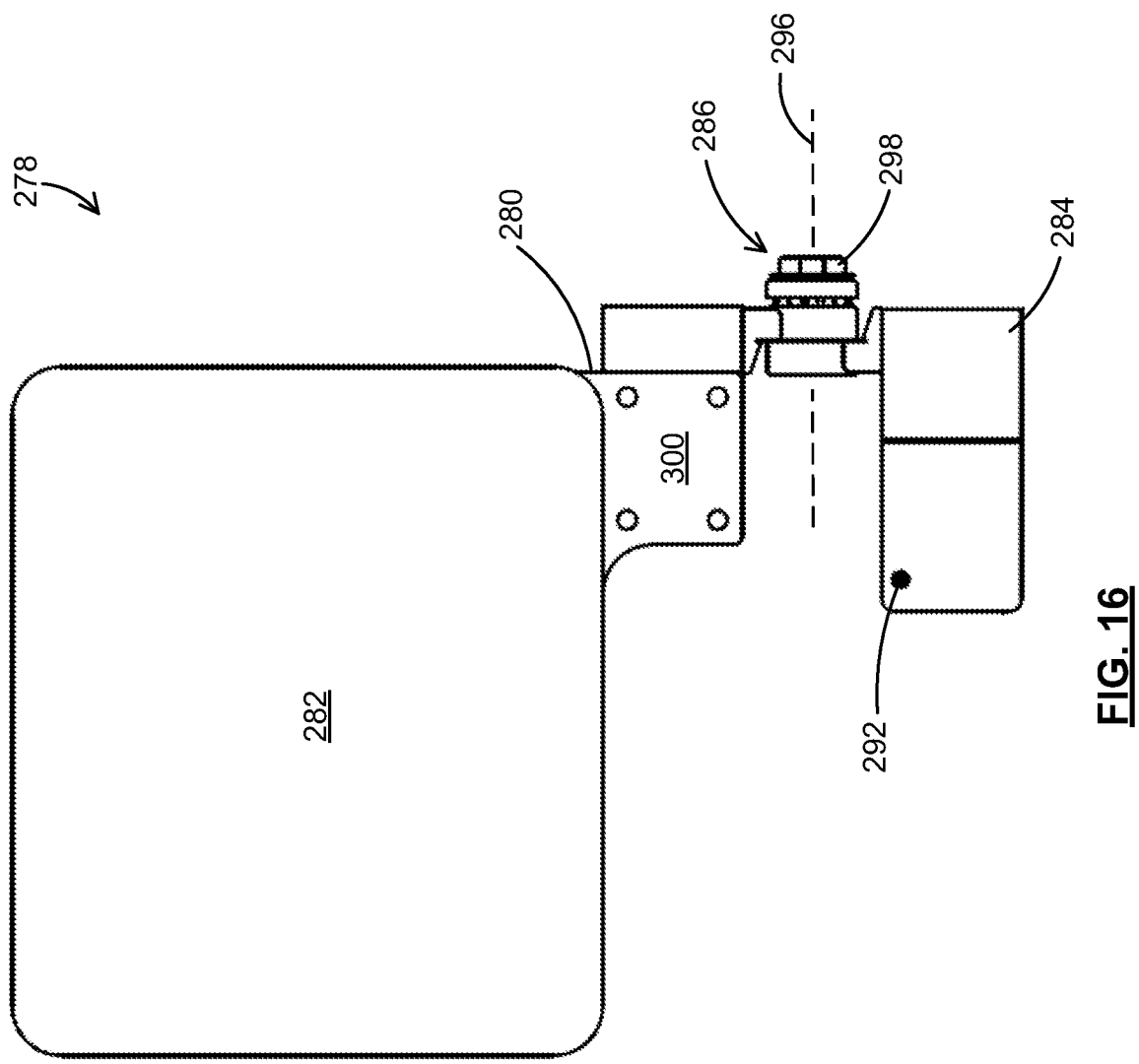
FIGS. 16, 17 and 18 are top, side and end views, respectively, of the pivotable arm support of FIG. 15.

The adjustable screen assembly 106 can be mounted to the board 102 either before or after the patient is positioned on the procedure table. The mount 190 includes at least one peg that can engage with any one of the apertures 132 to mount the adjustable screen assembly 106 to the board 102. Referring to FIG. 14, the mount 190 as illustrated includes a single peg 194. The adjustable screen assembly 106 can be mounted to the board 102 (FIG. 1) by engaging the peg 194 of the mount 190 with any one of the apertures 132 in the board 102. Accordingly, in the illustrated example, the bracket 182 can be mounted at multiple locations along either of the first, third and fourth board edges 120, 124, 126. For example, FIG. 2 shows the mount 190 mounted at the board edge 126 with the peg 194 engaged with the aperture $132_1$.

Referring again to FIG. 14, the peg 194 as illustrated extends downwardly and perpendicularly from the mount 190. The peg 194 is configured to be received in the insertion region 144 of any one of the apertures 132 and slidably engaged with one of the retention regions 142 of that aperture. As previously described, the reduced size of the retention regions 142 compared to the insertion region 144 can prevent the peg 194 from disengaging the aperture 132 (unless slid back to the insertion region 144).

Referring still to FIG. 14, the mount 190 as illustrated includes an alignment flange 198. The alignment flange 198 extends downwardly and perpendicularly from the mount 190. While mounting the bracket 182 to the board 102, the alignment flange 198 is received in a corresponding alignment slot 146. Which alignment slot 146 receives the alignment flange 198 of the mount 190 depends on which one of the apertures 132 in the board 102 receives the peg 194. To ensure fit, the arrangement of the peg 194 and the alignment flange 198 of the mount 190 correspond to the arrangement of the apertures 132 and the alignment slots 146 in the board 102. This can allow the mount 190 to be mounted at multiple locations along either of the first, third and fourth board edges 120, 124, 126. For example, FIG. 2 shows the mount 190 mounted along the board edge 126 with its alignment flange 198 received in the alignment slot $146_1$. The peg 194 and alignment flange 198 can cooperate to simplify installation and/or improve the stability of the connection between the mount 190 and the board 102. In some examples, the mount 190 may not include an alignment flange 198.

Referring to FIG. 14, the mount 190 as illustrated includes a compression screw 200. Once the bracket 182 is mounted to the board 102, e.g. as described above, the compression screw 200 can be tightened into the board 102. The threaded openings 175 (shown in FIGS. 4 and 5) in the board 102 are specifically located to receive the compression screw 200 of the mount 190. In this way, the compression screw 200 may be used to limit relative movement between the bracket 182 and the board 102, thereby stabilizing the connection between the adjustable screen assembly 106 and the board 102. Tightening compression screw 200 into the board 102 can also limit unintentional dismounting of the bracket 182 from the board 102. The compression screw 200 can be loosened prior to dismounting the bracket 182 from the board 102. In some examples, the bracket 182 may not include a compression screw 200.

Figure 11:
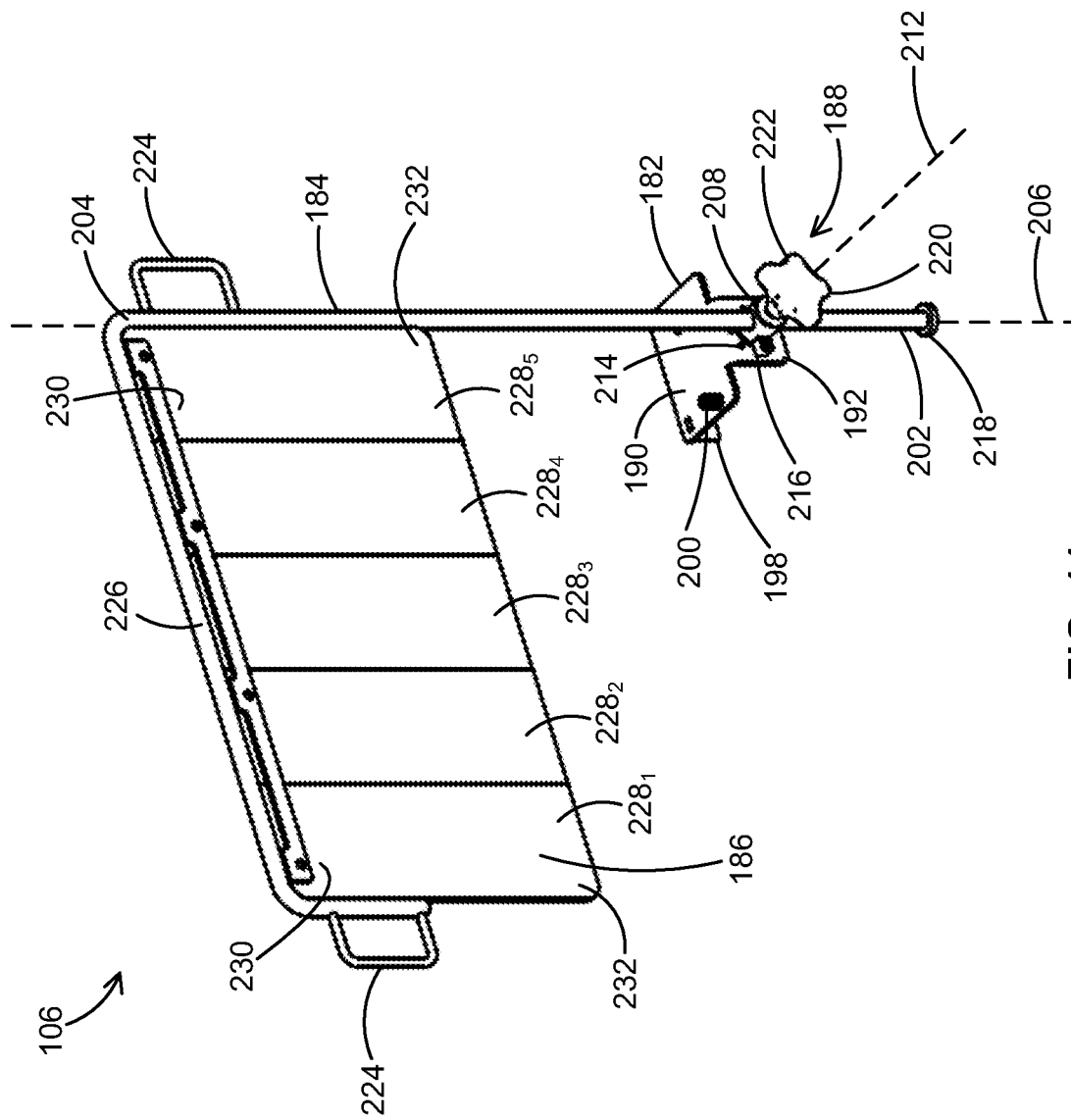
FIG. 11 is a perspective view of an example adjustable screen assembly having a shaft shown in an upright position.

Referring to FIG. 11, the shaft 184 extends between first and second shaft ends 202, 204 along a shaft axis 206. The screen 186 is connected to and supported by the shaft 184. As shown, the screen 186 extends perpendicularly from the shaft 184 proximate to the second shaft end 204. The clamping mechanism 188 is attached to the ledge 192 of bracket 182. The clamping mechanism 188 is configured to clamp the shaft 184 to maintain a position of the screen 186 above the board 102 (e.g. FIG. 1).

In the illustrated example, the clamping mechanism 188 includes a rotary joint 208. As shown in FIG. 14, the rotary joint 208 has a shaft opening 210 in which the shaft 184 is received. The rotary joint 208 is rotatable relative to the ledge 192 about a rotation axis 212 (FIG. 11) that is orthogonal to the shaft axis 206. The rotary joint 208 can be rotated about the rotation axis 212 to vary an angle between the shaft 184 and the bracket 182. For example, FIGS. 12 and 13 show the shaft 184 at different angles relative to the mount 190 of the bracket 182. In use, varying the angle between the shaft 184 and the bracket 182 adjusts the position of the screen 186 above the board 102 (e.g. see FIGS. 1 and 3).

Referring to FIG. 11, the ledge 192 includes a plurality of holes 214 arranged circumferentially around the rotary joint 208. The clamping mechanism 188 includes a tack 216 which can engage with any one of the holes 214 in the ledge 192. As shown, the tack 216 projects radially from the rotary joint 208 so as to rotate concurrently with the rotatory joint 208. In the illustrated example, the tack 216 includes a spring-loaded ball bearing that can be received within any one of the holes 214 when they are appropriately aligned. While the ball bearing of the tack 216 is received within one of the holes 214, an angle between the shaft 184 and the mount 190 is maintained. This angle is determined by which one of the holes 214 in the ledge 192 is engaged by the tack 216. The shaft 184 can be rotated about the rotation axis 212 by supplying a force that is sufficient to disengage the ball bearing of the tack 216 from the hole 214 in which it is received. The tack 216 can be used to maintain the shaft 184 in at least two angles relative to the mount 190 of the bracket 182. All else being equal, the greater the number of holes 214 arranged circumferentially around the rotary joint 208, the greater number of angles in which the shaft 184 can be maintained relative to the mount 190.

FIG. 12 shows the tack 216 holding the shaft 184 in an upright position in which an angle $\theta_1$ between the shaft 184 and the mount 190 is about 90°. FIG. 13 shows the tack 216 holding the shaft 184 in an angled position in which an angle $\theta_2$ between the shaft 184 and the mount 190 is about 45°. To adjust the position of the screen 186, one can vary the angle between the shaft 184 and the mount 190 by engaging the tack 216 with a different hole 214 in the ledge 192. The operator can push the screen 186 out of the field of view when needing to visualize an area of interest and then easily and reliably reposition the screen 186 back to the initial protective position. This can be particularly advantageous during medical procedures in which the screen 186 is often moved in and out of the field of view multiple times (e.g. during a pacemaker implantation). For example, the screen 186 can be alternated between an unobstructed position for direct visualization and a radiation shielding position during fluoroscopy.

In the illustrated example, the shaft 184 can be rotated about the shaft axis 206 to vary an angle between the screen 186 and the bracket 182. That is, the shaft 184 can spin within the shaft opening 210. In use, varying the angle between the screen 186 and the bracket 182 adjusts the position of the screen 186 above the board 102. Accordingly, in the illustrated example, the shaft 184 is adjustable with at least two rotational degrees of freedom relative to the bracket 182 (i.e. it rotates about at least the shaft axis 206 and the rotation axis 212).

In the illustrated example, the shaft 184 can be translated through the shaft opening 210 to vary a distance between the screen 186 and the mount 190 of the bracket 182. In use, varying the distance between the screen 186 and the bracket 182 adjusts the position of the screen 186 above the board 102. This can allow one performing the procedure to adjust position of the screen 186 according to his or her height. As best shown in FIG. 14, the first shaft end 202 includes a stopper 218 having a diameter larger than that of the shaft opening 210. Accordingly, the stopper 218 can prevent the shaft 184 from being pulled through the shaft opening 210 while adjusting the distance between the screen 186 and the bracket 182.

Referring still to FIG. 14, the clamping mechanism 188 includes a compression screw 220. The compression screw 220 can be tightened into the shaft 184 via a threaded hole in the rotary joint 208 to restrict translation and rotation of the shaft 184 in the shaft opening 210. As needed, the compression screw 220 can be loosened to allow translation and rotation of the shaft 184 in the shaft opening 210. In the illustrated example, the compression screw 220 includes an oversized grip 222 at its head to facilitate tightening and loosening.

The screen 186 can include one or more grips or handles to facilitate adjusting its position relative to the board 102. Alternatively, or in addition, the one or more grips or handles can facilitate mounting the adjustable screen assembly 106 to the board 102. In the illustrated example, the screen 186 includes a pair of handles 224 that extend from opposite sides of the screen 186. Specifically, the handle 224 farthest from the shaft 184 can be used to push and pull the screen 186 in and out of the field of view. Alternatively, in some examples, handles 224 may not be provided.

With reference to FIGS. 11 to 13, the screen 186 includes a frame member 226 extending away from the shaft axis 206 and a plurality of strips 228 suspended from the frame member 226. In the illustrated example, the frame member 226 is integral with the second shaft end 204 and extends generally perpendicularly from the shaft axis 206, thereby giving the shaft 184 and the frame member 226 an L-shape appearance. Each of the strips 228 extend between opposed first and second strip edges 230, 232. The first strip edges 230 are connected to the frame member 226 so that each of the strips 228 can tilt out of the field of view when the screen 186 is pushed aside. The first strips edges 230 can be mounted to the frame member 226 by one or more mechanical fasteners, e.g. screws, clamps, etc. In some examples, the strips 228 can be removed and/or replaced as needed.

The strips 228 have a strip length between the first and second strip edges 230, 232. The strip length can be between about 10 cm and about 60 cm, or between about 20 cm and about 50 cm. These dimensions are intended to be illustrative but non-limiting. In use, the strips 228 impede passage of radiation scatter directed at the head and/or neck of the individual performing the medical procedure.

The strips 228 can be formed at least partially of substantially radiopaque material, e.g. for example, lead, tin, antimony, tungsten or bismuth. In some examples, the strips 228 are formed of vinyl coated lead rubber. In some examples, the strips 228 are formed of the same material as shield members 154 (FIG. 6). In some examples, the strips 228 can be partially overlapped to avoid any gap being defined between them. In the illustrated example, five strips $228_{1-5}$ are arranged continuously along the frame member 226. In one or more alternative examples, more (e.g. 6 to 10) or less strips 228 (e.g. one) may be suspended from the frame member 226.

In some examples, the strips 228 are flexible along the entire strip length. The flexibility of the strips 228 can provide more room for hands to manipulate equipment under the screen 186, while maintaining a high level of protection from radiation scatter.

Referring again to FIGS. 1 to 3, the skirt 108 is shown mounted to the board 102 to shield radiation scatter below the procedure table. As shown, the skirt 108 includes a panel 234. The panel 234 can be formed at least partially of substantially radiopaque material, e.g. for example, lead, tin, antimony, tungsten or bismuth. In some examples, the panel 234 is formed of a unitary piece of vinyl coated lead rubber. In some examples, the panel 234 is formed of the same material as the strips 228 (FIG. 11) and/or the shield members 154 (FIG. 6).

The skirt 108 can be mounted to the board 102 either before or after the patient is positioned on the procedure table. The skirt 108 includes at least one peg that can engage with any one of the apertures 132. Referring to FIG. 1, the skirt 108 as illustrated includes a pair of spaced apart pegs 236. The stability of the connection between the panel 234 and the board 102 can be improved by spacing the pegs 236 apart, e.g. as shown. To ensure fit, the distance between the pegs 236 of the skirt 108 can correspond to the distance between multiple pairs of the apertures 132 in the board 102. For example, if the distance between the pegs 236 is 60 cm, the board 102 can have a plurality of aperture pairs that are similarly spaced apart by 60 cm.

In the illustrated example, the pegs 236 extend upwardly and perpendicularly from a top end of the panel 234. The pegs 236 are configured to be received in the insertion region 144 of corresponding apertures 132 and slidably engaged with one of the retention regions 142 of those apertures. As previously described, the reduced size of the retention regions 142 compared to the insertion region 144 can prevent the pegs 236 from disengaging the apertures 132 (unless slid back to the insertion regions 144).

In the illustrated example, the skirt 108 can be mounted at multiple locations along either of the third and fourth board edges 124, 126. For example, FIG. 3 shows the skirt 108 mounted along the third board edge 124. The apertures 132 engaged by the pegs 236 can also be located laterally across from each other on opposite board edges 124, 126. That is, one of the apertures 132 engaged by the pegs 236 of the skirt 108 can be located at the third board edge 124 and the other of the apertures 132 engaged by pegs 236 of the skirt 108 can be located at the fourth board edge 126. For example, FIG. 1 shows the skirt 108 mounted to the board

102 with its pegs 236 correspondingly received in the apertures 132₁ at respective board edges 124, 126. While in this position, the skirt 108 may shield a staff member stationed at the patient's head from radiation scatter below the procedure table.

The skirt 108 can be mounted to the board 102 in a position where it is well suited to protect those in attendance from below table radiation scatter. In some cases, two or more skirts 108 can be mounted to the board 102 at the same time to offer more protection. This can be particularly advantageous in cases where staff members are stationed in multiple locations around the procedure table.

Referring to FIG. 1, the panel 234 has a panel height in the vertical direction 118. The panel height can correspond to the distance between the top of the procedure table and the floor. In some examples, the panel 234 extends all the way to the floor. The panel height can between about 50 cm and about 100 cm, or between about 60 cm and about 80 cm. These dimensions are intended to be illustrative but non-limiting.

The skirt 108 can include one or more handles or grips to facilitate its mounting and/or dismounting from the board 102. In the illustrated example, the skirt 108 includes a pair of handles 238 that extend outwardly from opposite sides of the panel 234. Alternatively, in some examples, handles 238 may not be provided.

Referring again to FIGS. 1 to 3, the shielded arm support 110 is shown mounted to the board 102 to support one of the patient's arms and/or shield one of more attending staff members from radiation scatter during the medical procedure. In some examples, the apparatus 100 can include features of the arm support apparatuses disclosed in International Publication No. WO 2019/227210 A1, the entire contents of which are hereby incorporated herein by reference. As shown, the shielded arm support 110 includes a base 240, an arm pad 242, a first barrier 244 and a second barrier 246. In use, the arm pad 242 supports one of the patient's arms, and the first and second barriers 244, 246 can shield an attending staff member from scatter radiation during the medical procedure.

The shielded arm support 110 can be mounted to the board 102 either before or after the patient is positioned on the procedure table. The base 240 includes at least one peg that can engage with any one of the apertures 132 to mount the shielded arm support 110 to the board 102. Referring to FIG. 2, the base 240 as illustrated includes a pair of spaced apart pegs 274. The base 240 as illustrated also includes an alignment flange 276. In mounting the base 240 to the board 102, the pegs 274 and alignment flange 276 can function in a similar fashion as the pegs 166 and the alignment flange 168 of the track 152 described above. In the illustrated example, the base 240 can be mounted at multiple locations along either of the third and fourth board edges 124, 126. For example, FIG. 1 shows the base 240 mounted along the third board edge 124, while FIG. 3 shows the base 240 mounted along the fourth board edge 126.

In some examples, the base 240 can include a compression screw (not shown, but can be similar to the compression screw 170 of the track 152 in FIG. 10). The compression screw may be used to limit relative movement between the base 240 and the board 102 thereby stabilizing the connection between the shielded arm support 110 and the board 102.

In the illustrated example, the arm pad 242 is positioned on the base 240. The arm pad 242 extends in the longitudinal direction 114 between first and second pad ends 248, 250. In some examples, the arm pad 242 can rest on the base 240, without being attached. This can allow adjustment of the position of the arm pad 242 according to patient's arm length. Accordingly, in these cases, the position of the arm pad 242 can be customized to the patient's size without needing to move the patient and/or the base 240 underneath. In other examples, the arm pad 242 can be fixed to the base 240.

Referring to FIG. 1, the base 240 extends in the lateral direction 116 between a first base edge 252 and a second base edge 254 to support a width of the arm pad 242. The first base edge 252 is hidden from view in FIG. 1, but is shown in FIG. 3. The first and second barriers 244, 246 are mounted to the first and second base edges 252, 254, respectively. The first barrier 244 can be mounted to the base 240 by a flexible and resilient connection (e.g. a curved bracket formed of spring steel) to permit adjustment of its position.

The first barrier 244 extends upwardly from the first base edge 252 in the vertical direction 118 to above the arm pad 242. The second barrier 246 extends downwardly from the second base edge 254 in the vertical direction 118. As shown, the arm pad 242 is positioned laterally intermediate the first and second barriers 244, 246. The first and second barriers 244, 246 are each shown to be generally planar and arranged vertically. The first and second barriers 244, 246 can each be formed at least partially of a substantially radiopaque material, e.g. lead, tin, antimony, tungsten, or bismuth. In some examples, the first and second barriers 244, 246 are formed of vinyl coated lead sheets.

The arm pad 242 as illustrated includes a proximal portion 256 at the first pad end 248, a distal portion 258 at the second pad end 250, and a central portion 260 arranged between the proximal and distal portions 256, 258. In use, the proximal portion 256 supports an arm of the patient, and the central portion 260 supports a hand of that arm. The portions 256, 258, 260 each include an upper surface 262, 264, 266, respectively. In the illustrated example, each of the upper surfaces 262, 264, 266 is spaced above the base 240 in the vertical direction 118.

Referring still to FIG. 1, it can be seen that the upper surface 266 of the central portion 260 is substantially below the upper surface 262 of the proximal portion 256. In the illustrated example, the upper surface 266 of the central portion 260 is concave in shape so that the patient's hand can be positioned below their arm. The upper surface 264 of the distal portion 258 is shown to be generally planar and horizontal, and can be used by the attending staff as a working surface. In some examples, the upper surface 264 of the distal portion 258 can be reinforced to create a stable working surface.

Referring still to FIG. 1, the base 240 extends in the longitudinal direction 114 to support a length of the arm pad 242. The first and second barriers 244, 246 are each shown arranged longitudinally intermediate of the arm pad 242. Furthermore, the central portion 260 of the arm pad 242 is shown arranged within a longitudinal extent of each of the first and second barriers 244, 246. With this arrangement, in use, the first and second barriers 244, 246 provide radiation shielding in the vicinity of the hand of the patient.

In some examples, the arm pad 242 can be formed of a foam material that is clad with marine grade vinyl. The base 240 can be formed at least partially of a substantially radiolucent material. In some examples, the base 240 can be formed of a unitary piece of clear polycarbonate material.

Figure 20:
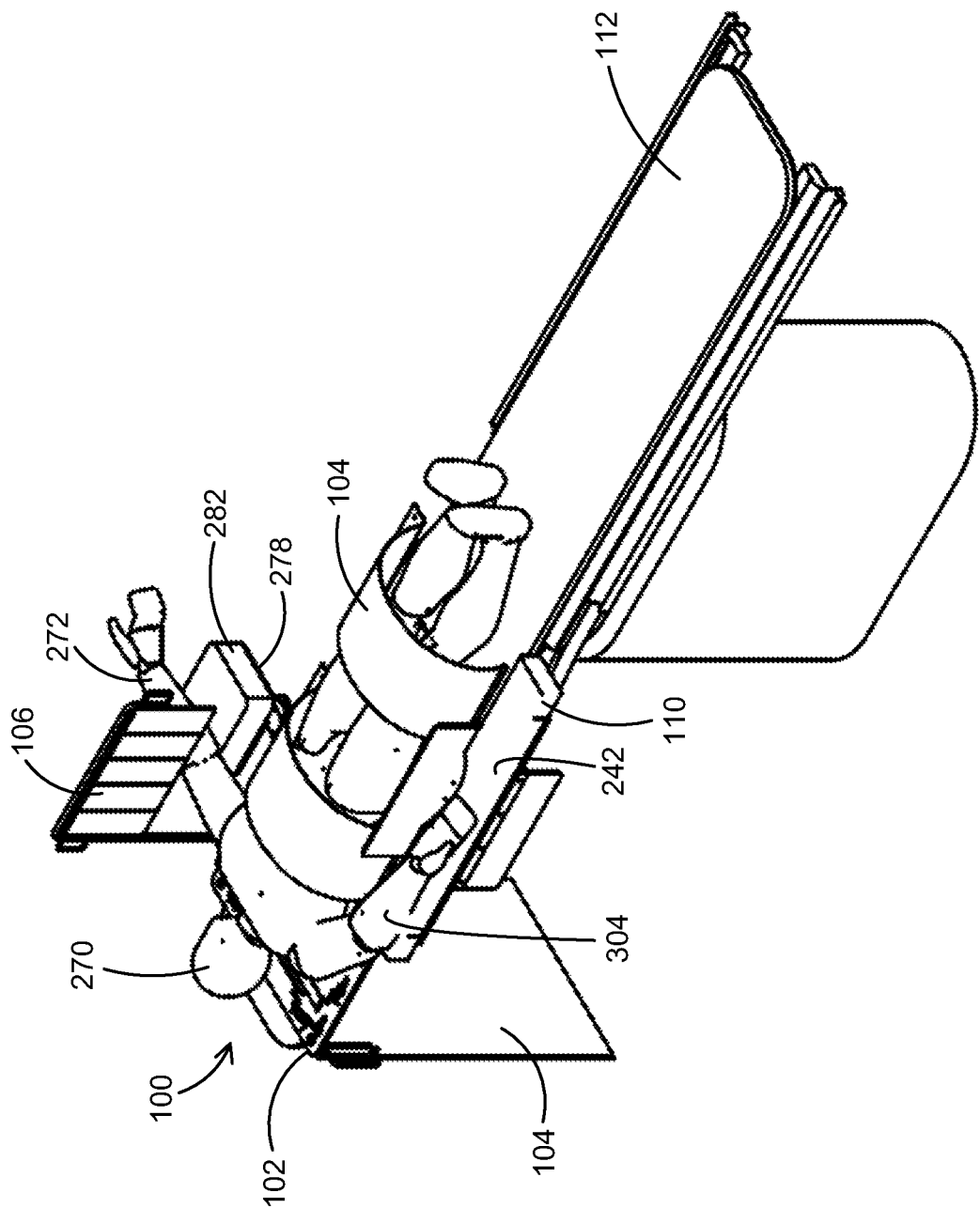
FIGS. 20 and 21 are perspective views of the apparatus of FIG. 1 showing a patient supported by a procedure table, with the pivotable arm support of FIG. 13 shown in different positions.

Referring to FIGS. 20 and 21, the shielded arm support 110 is shown supporting a right arm 304 of a patient 270 that is lying on a procedure table 112. The shielded arm support 110 can provide several advantages. These advantages relate to: increased radiation protection, improved visualization, greater operator convenience, and enhanced patient comfort.

In terms of increased radiation protection, the first and second radiation barriers 244, 246 can be substantially radiopaque, and can block significantly more radiation than existing shielding equipment. The shielded arm support 110 can also be compatible with femoral access procedures, and provide radiation protection for such cases.

In terms of improved visualization, the polycarbonate base 240 can be more radiolucent than existing devices, which can reduce the amount of radiation needed during medical imaging. Furthermore, the position of the base 240 along one of the third and fourth board edges 124, 126 is outside of the typical field of view (the patient's chest), which can prevent both increases in radiation and image degradation. Moreover, the positioning of the radiation barriers 244, 246 can allow clear fluoroscopic visualization of the patient's arm.

In terms of operator convenience, beyond the patient's hand, the working surface of the distal portion 258 of the arm pad 242 can be level with the patient's wrist and provide a convenient platform upon which the attending staff can manipulate equipment. Furthermore, the contoured shapes of the upper surfaces 262, 264 of the proximal and central portions 256, 260 of the arm pad 242 can position the patient's wrist at a desirable angle, improving the attending staff's access to the patient's artery. Moreover, because the shielded arm support 110 can be compatible with both radial and femoral access cases, the shielded arm support 110 does not need to be removed between cases depending on the access site chosen.

Finally, the arm pad 242 can be relatively large and include contoured foam padding to provide full arm support and enhance patient comfort. Furthermore, the flexibility of the first barrier 244 allows for multiple positions to accommodate the patient, and because it is not rigidly attached to the base 240 it has some give if it is struck by the patient or the attending staff.

Reference is now made to FIGS. 15 to 19, which illustrate a pivotable arm support, referred to generally as 278, for supporting one of the patient's arms. As shown, the pivotable arm support 278 includes an adjustable support 280, an arm pad 282, a mounting bracket 284 and a hinge mechanism, referred to generally as 286. The adjustable support 280 is coupled to the mounting bracket 284 by the hinge mechanism 286. In use, the arm pad 282 supports one of the patient's arms. In some examples, the adjustable support 280 can be formed at least partially of substantially radiopaque material, e.g. for example, lead, tin, antimony, tungsten or bismuth. In some examples, the adjustable support 280 can be formed of vinyl coated lead rubber.

Figure 17:
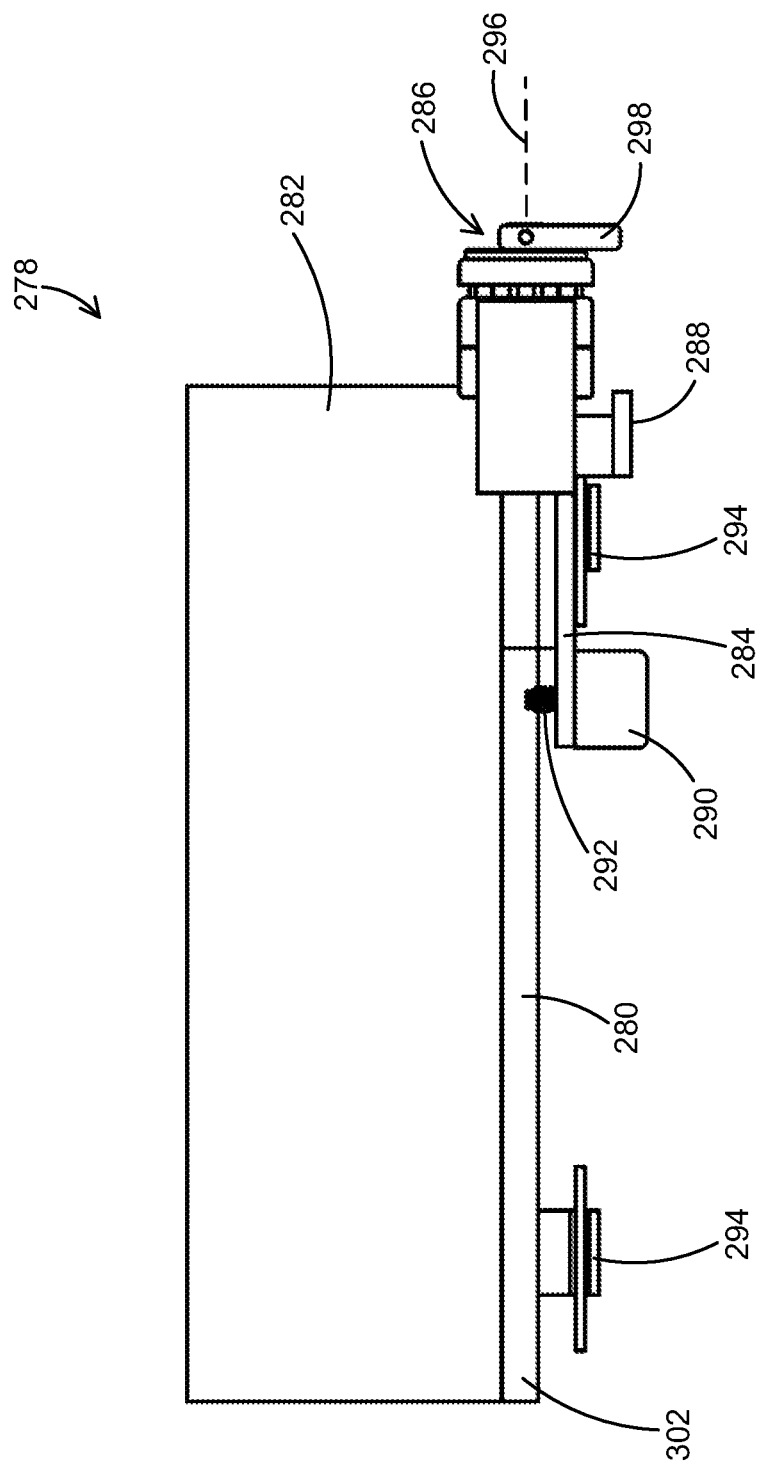
Figure 18:
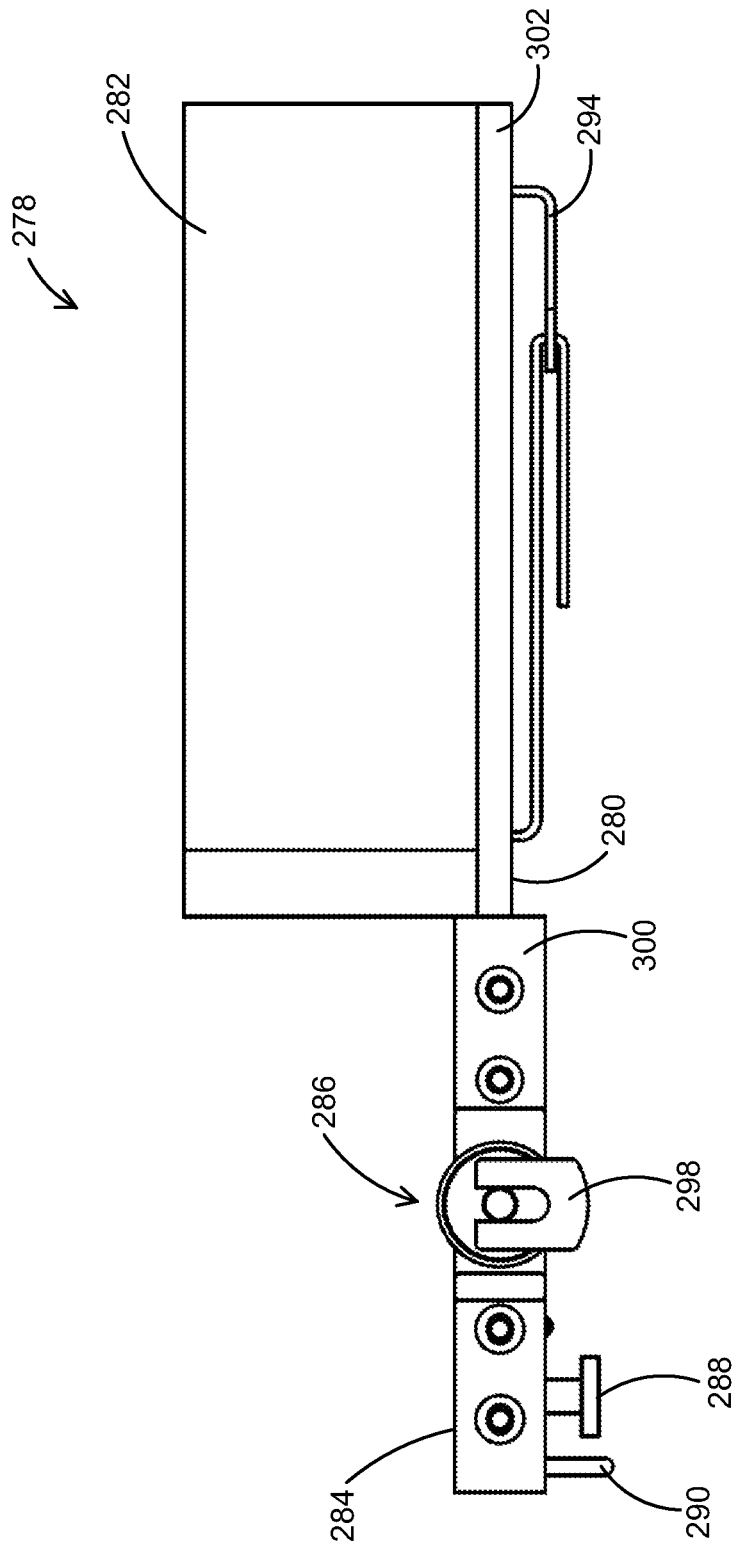

The pivotable arm support 278 can be mounted to the board 102 either before or after the patient is positioned on the procedure table. The mounting bracket 284 includes at least one peg that can engage with any one of the apertures 132 to mount the pivotable arm assembly 278 to the board 102. Referring to FIGS. 17 and 18, the mounting bracket 284 as illustrated includes a single peg 288. The pivotable arm support 278 can be mounted to the board 102 (FIG. 1) by engaging the peg 288 of the mounting bracket 284 with any one of the apertures 132 in the board 102. As such, in the illustrated example, the mounting bracket 284 can be mounted at multiple locations along either of the third and fourth board edges 124, 126. For example, FIG. 2 shows the mounting bracket 284 mounted at the fourth board edge 126 with the peg 288 engaged with the aperture $132_4$.

Referring again to FIGS. 17 and 18, the peg 288 as illustrated extends downwardly and perpendicularly from the mounting bracket 284. The peg 288 is configured to be received in the insertion region 144 of any one of the apertures 132 and slidably engaged with one of the retention regions 142 of that aperture. As previously described, the reduced size of the retention regions 142 compared to the insertion region 144 can prevent the peg 288 from disengaging the aperture 132 (unless slid back to the insertion region 144).

Referring still to FIGS. 17 and 18, the mounting bracket 284 as illustrated includes an alignment flange 290. The alignment flange 290 extends downwardly and perpendicularly from the mounting bracket 284. While mounting the mounting bracket 284 to the board 102, the alignment flange 290 is received in a corresponding alignment slot 146. Which alignment slot 146 receives the alignment flange 290 of the mounting bracket 284 depends on which one of the apertures 132 in the board 102 receives the peg 288. To ensure fit, the arrangement of the peg 288 and the alignment flange 290 of the mounting bracket 284 correspond to the arrangement of the apertures 132 and the alignment slots 146 in the board 102. This can allow the mounting bracket 284 to be mounted at multiple locations along either of the third and fourth board edges 124, 126. For example, FIG. 2 shows the mounting bracket 284 mounted along the fourth board edge 126 with its alignment flange 290 received in the alignment slot $146_3$. The peg 288 and alignment flange 290 can cooperate to simplify installation and/or improve the stability of the connection between the mounting bracket 284 and the board 102. In some examples, the mounting bracket 284 may not include an alignment flange 290.

Referring to FIG. 17, the mounting bracket 284 as illustrated includes a compression screw 292. Once the mounting bracket 284 is mounted to the board 102, e.g. as described above, the compression screw 292 can be tightened into the board 102. The threaded openings 175 (shown in FIGS. 4 and 5) in the board 102 are specifically located to receive the compression screw 292 of the mounting bracket 284. In this way, the compression screw 292 may be used to limit relative movement between the mounting bracket 284 and the board 102, thereby stabilizing the connection between the pivotable arm support 278 and the board 102. Tightening the compression screw 292 into the board 102 can also limit unintentional dismounting of the mounting bracket 284 from the board 102. The compression screw 292 can be loosened prior to dismounting the mounting bracket 284 from the board 102. In some examples, the mounting bracket 284 may not include the compression screw 292.

The adjustable support 280 is shown to be generally planar. As shown in FIG. 2, the support 280 includes a central cutout 306, intended to reduce weight. The arm pad 282 is positioned on the support 280. Referring to FIGS. 17 and 18, the arm pad 282 as illustrated is secured to the support 280 with a pair of straps 294. The support 280 includes two pairs of laterally spaced apart slits 308 (shown in FIG. 2), which are designed to accept the straps 294 to secure the arm pad 282 to the support 280. In some examples, the arm pad 282 can be secured to either side of the support 280, thereby improving versatility.

Figure 19:
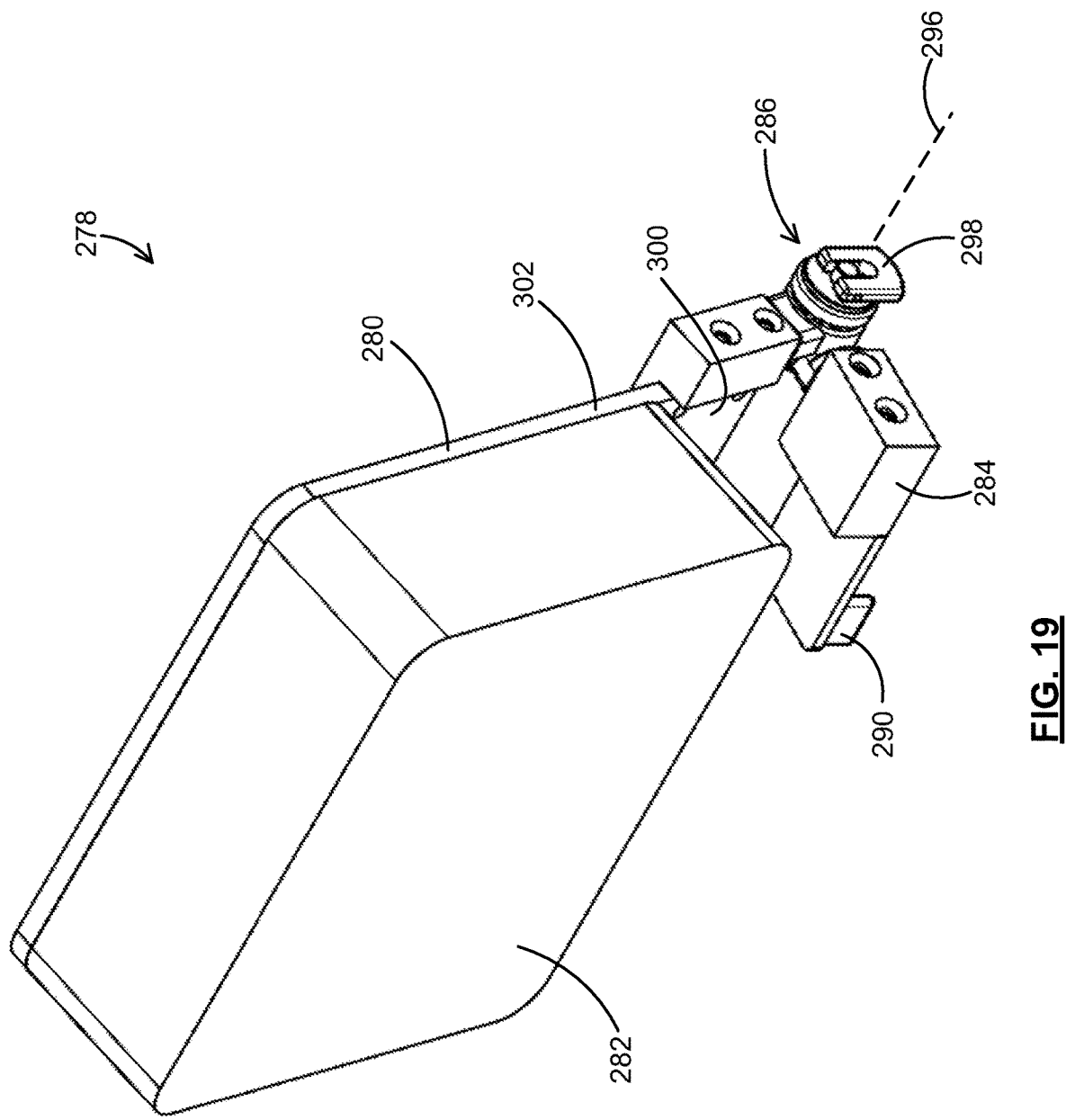
FIG. 19 is a perspective view of the pivotable arm support of FIG. 15, shown in an upright position.

The support 280 can be pivoted about a longitudinal axis 296 by actuating a tab 298. The tab 298 disengages locks in the hinge mechanism 286 to permit pivoting of the support 280 about the longitudinal axis 296. Releasing the tab 298 reengages the locks to fix the support 280 at a desired angle relative to the mounting bracket 284. In the illustrated example, the tab 298 is provided at the hinge mechanism 286. This can allow for one handed adjustment of the support 280. FIGS. 15 to 18 show the support 280 and the arm pad 282 in a generally horizontal position (i.e. the angle between the support 280 and the mounting bracket is about 180°). FIG. 19 shows the support 280 and the arm pad 282 in an upright position (i.e. the angle between the support 280 and the arm pad 282 is about 80 to 90°). As previously described, while pivoting the support 280 about the longitudinal axis 296, the tab 298 can be released to reengage the locks to fix the support 280 at any angle between the generally horizontal position and the upright position.

In the illustrated example, the support 280 has a relatively narrow proximal portion 300 adjacent to the hinge mechanism 286 and relatively large distal portion 302. This arrangement may be less intrusive when pivoted upwardly towards the patient, e.g. as shown in FIG. 21. The distal portion 302 of the support 280 can be appropriately sized to support a length and a width of the arm pad 282.

In some cases, the pivotable arm support 278 and the shielded arm support 110 can be mounted on opposite board edges 124, 126. That is, one supports the patient's left arm while the other supports the patient's right arm. This can be particularly useful during medical procedures where access to both right and left radial arteries of the patient is required. In other cases, the pivotable arm support 278 and the shielded arm support 110 can be mounted on the same board edge 124, 126 (e.g. FIG. 22). This arrangement can allow the patient's arm to be fully abducted while supported on the pivotable arm support 278 when obtaining radial access. Subsequently, the patient's arm can be adducted to the patient's side where it rests on the shielded arm support 110 for the remainder of the medical procedure.

FIG. 20 shows the arm pad 282 and the support 280 in a generally horizontal position. The arm pad 282 is shown supporting a left arm 272 of the patient 270 during a medical procedure, in which the left radial artery of the patient 270 can be accessed, for example. At the same time, the arm pad 242 of the shielded arm support 110 is shown supporting a right arm 304 of the patient 270. During the medical procedure, an attending staff member can remain along the right hand side relative to the patient 270, and the shielded arm support 110 can therefore continue to shield this attending staff member from radiation scatter.

FIG. 21 shows the support 280 in an upright position in which there is about an 80° angle between the support 280 and the mounting bracket 284. This can be a more comfortable position for the patient 270 to maintain, after the left radial artery has been accessed, and during which images can be taken using a C-arm camera, for example.

Reference is now made to FIGS. 22 to 29, which illustrate the apparatus 100 in exemplary configurations for a number of different medical procedures. The arrangement of the various radiation shields 104, 106, 108, 110 and the pivotable arm support 278 of the apparatus 100 shown across FIGS. 22 to 29 is intended for illustrative purposes. Owing the distribution of the apertures 132 in the board 102, there are many possible ways of configuring the apparatus 100.

Figure 23:
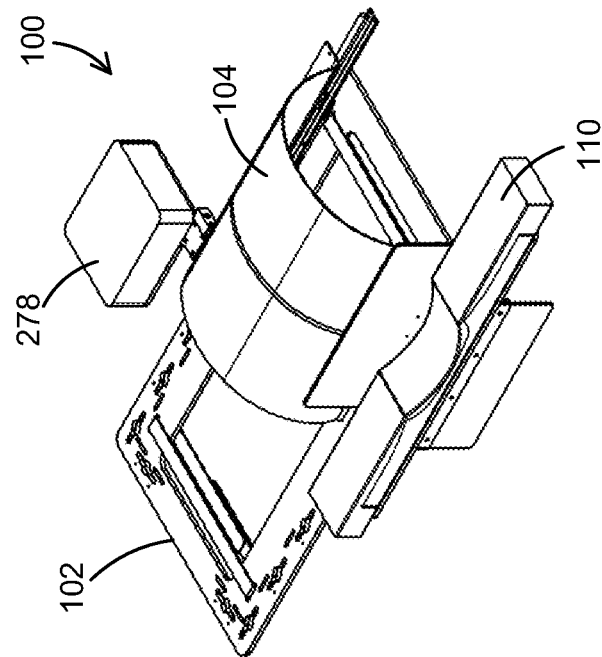
FIGS. 22 to 29 are perspective views of example apparatuses for shielding medical radiation, with the radiation shields of each apparatus shown positioned for a different type of medical procedure.
Figure 22:
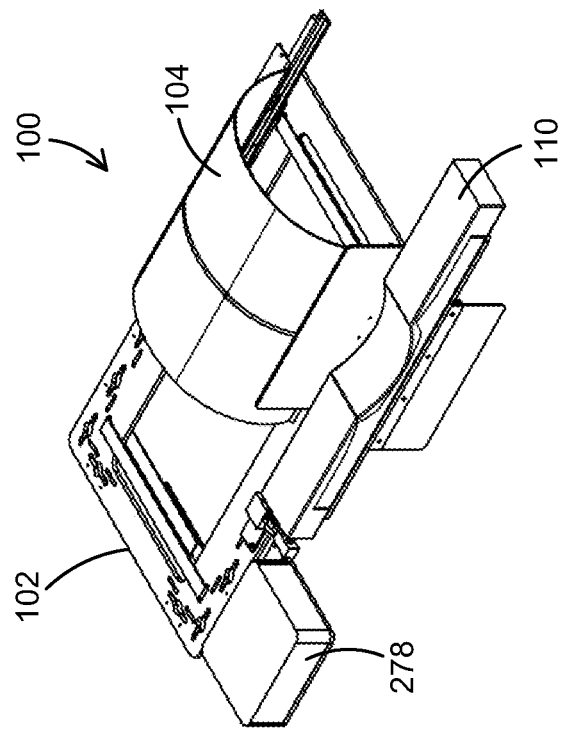
Figure 25:
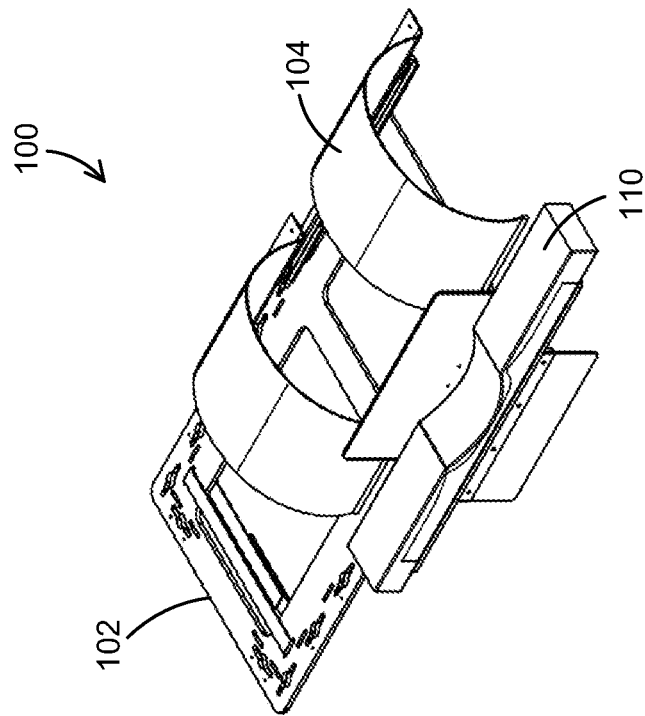
Figure 24:
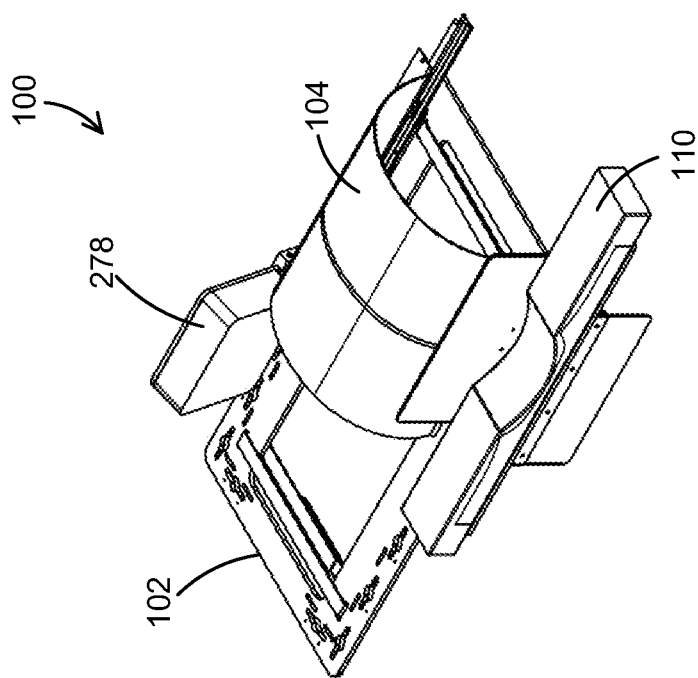
Figure 27:
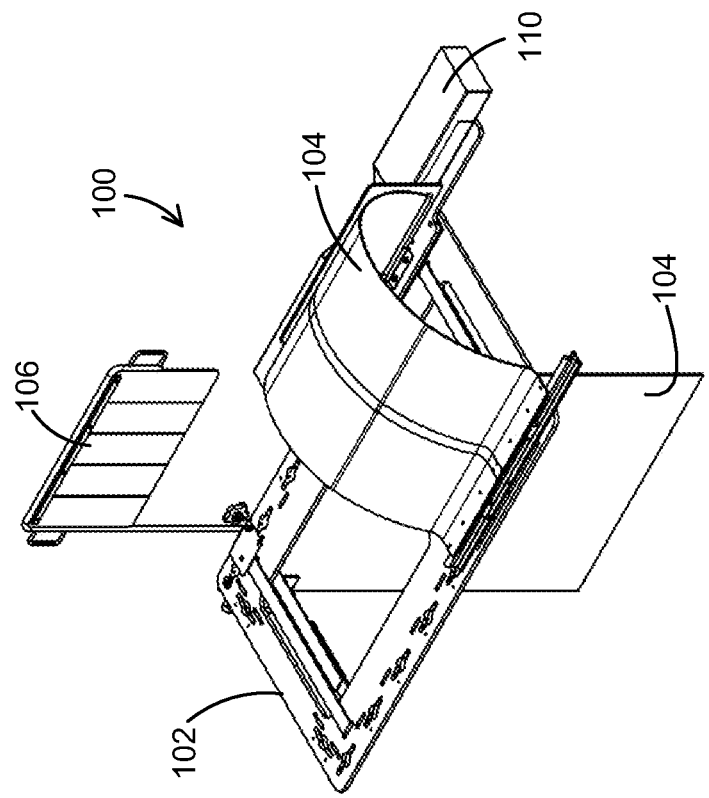
Figure 26:
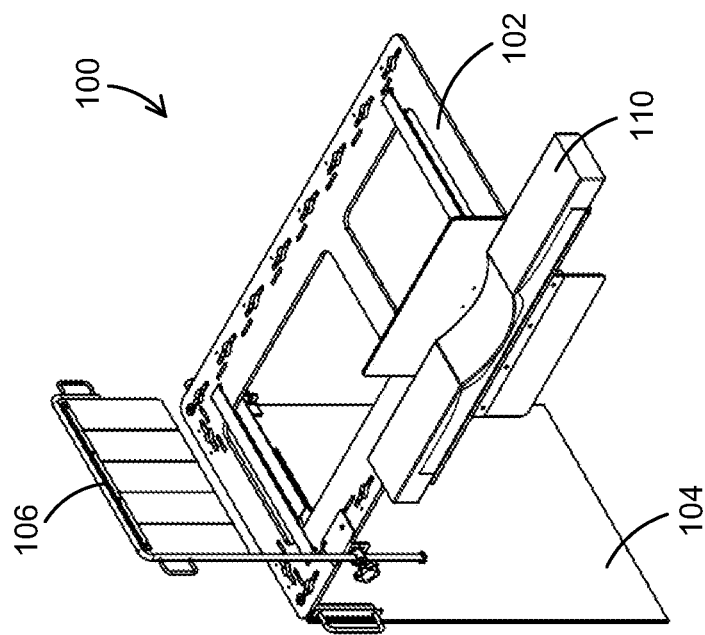

FIGS. 22 and 23 show the apparatus 100 configured for right and left radial access, respectively. FIG. 24 shows the apparatus 100 of FIG. 21 but with the pivotable arm support 278 in an upright position to support the patient's left elbow during a medical procedure in which the left radial artery is used for access. FIG. 25 shows the apparatus 100 configured for femoral artery access. FIG. 26 shows the apparatus 100 configured for structural heart procedures in which staff members would be positioned at both the patient's side and at the head of the procedure table. FIG. 27 shows the apparatus 100 configured for a medical procedure to implant a pacemaker or defibrillator where the operator would be positioned proximate to the patient's left shoulder. The configurations of the apparatus 100 shown in FIGS. 22 to 27 may be classified as "interventional cardiology" procedures.

Figure 29:
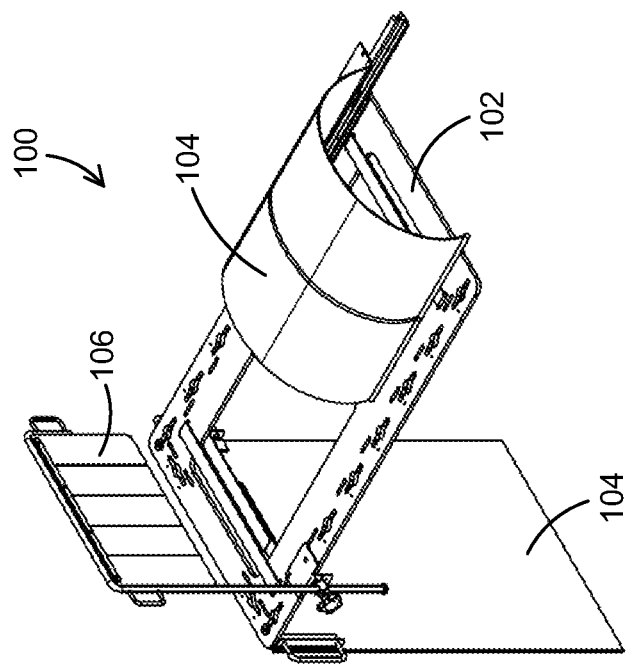
Figure 28:
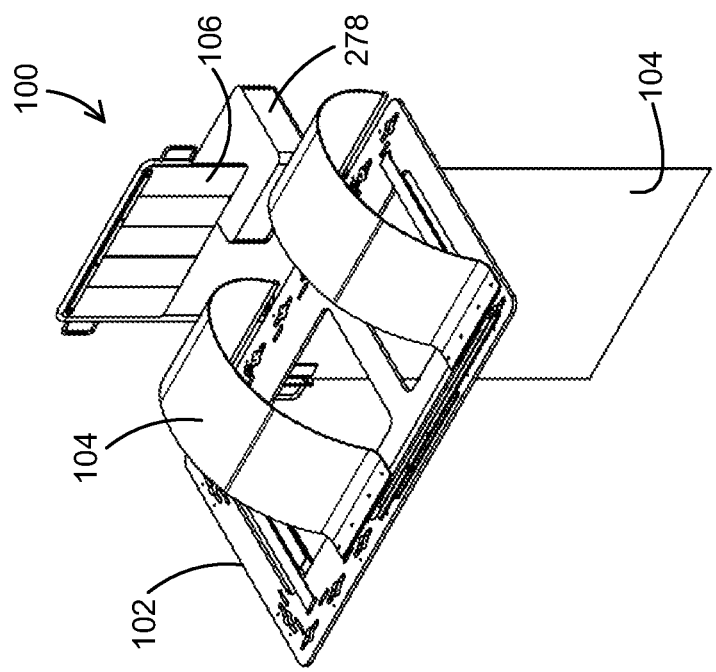

FIG. 28 shows the apparatus 100 configured for percutaneous endoscopic gastrostomy (PEG), a procedure in which a flexible feeding tube is placed through the abdominal wall and into the stomach. PEG allows nutrition, fluids and/or medications to be put directly into the stomach, bypassing the mouth and esophagus. FIG. 29 shows the apparatus 100 configured for a central venous line (CVL) insertion. The configurations of the apparatus 100 shown in FIGS. 28 and 29 may be classified as "interventional radiology" procedures.

While the above description provides examples of one or more apparatuses or methods, it will be appreciated that other apparatuses or methods may be within the scope of the accompanying claims.

We claim:

1. An apparatus for shielding radiation emitted during a medical procedure, the apparatus comprising:
   a board positionable on top of a procedure table, the board extending laterally between a first board edge and a second board edge, and longitudinally between a third board edge and a fourth board edge, the board comprising a plurality of apertures distributed along at least one of the board edges; and
   at least one radiation shield removably mountable to the board, the at least one radiation shield comprising at least one peg engageable with any one of the apertures in the board,
   wherein the board comprises a plurality of alignment slots distributed along at least one of the first and second board edges, and the at least one radiation shield comprises an alignment flange engageable with one of the alignment slots, and the alignment flange is engageable with the one of the alignment slots adjacent to the aperture engaged by the at least one peg of the at least one radiation shield.

2. The apparatus of claim 1, wherein the board has a first board side and an opposed second board side, each of the first and second board sides extending laterally between the first and second board edges, and the at least one peg of the at least one radiation shield is engageable with any one of the apertures in the board from either of the first or second board sides.

3. The apparatus of claim 2, wherein each of the plurality of apertures in the board comprise an opposed pair of retention regions extending away from an insertion region, the at least one peg of the at least one radiation shield is configured to be received in the insertion region of any one of the apertures and slidably engaged with one of the retention regions of that aperture, and each of the retention regions extends longitudinally from the insertion region.

4. The apparatus of claim 3, wherein the at least one radiation shield comprises a first radiation shield and a second radiation shield, and while the at least one peg of the first radiation shield is engaged with one of the retention regions of any one of the apertures in the board, and the at least one peg of the second radiation shield is engageable with the other of the retention regions of that aperture.

5. The apparatus of claim 1, wherein the plurality of apertures are distributed along each of the first and second board edges, the plurality of apertures are evenly distributed along each of the first and second board edges, and each one of the apertures distributed along the first board edge is longitudinally aligned with a corresponding one of the apertures distributed along the second board edge.

6. The apparatus of claim 5, wherein the at least one radiation shield comprises a body shield assembly for shielding a patient supported above the procedure table from radiation, and the body shield assembly comprises:
   a longitudinally extending track mountable to the board along one of the first and second board edges; and
   at least one shield member extending from a first shield edge to a second shield edge, the first shield edge being attached to and slidable along the track.

7. The apparatus of claim 1, wherein, while positioned on top of the procedure table, at least one of the first and second board edges project laterally beyond the procedure table to define a board overhang region, and each of the plurality of apertures are located within the board overhang region.

8. The apparatus of claim 1, wherein the at least one radiation shield comprises a body shield assembly for shielding a patient supported above the procedure table from radiation, and the body shield assembly comprises:
   a longitudinally extending track mountable to the board along one of the first and second board edges; and
   at least one shield member extending from a first shield edge to a second shield edge, the first shield edge being attached to and slidable along the track.

9. The apparatus of claim 8, wherein the at least one peg of the body shield assembly comprises longitudinally spaced apart first and second pegs extending from the track, the first and second pegs being correspondingly engageable with a pair of the apertures in the board, the at least one shield member has a shield width between the first and second shield edges, and the at least one shield member being flexible along the shield width.

10. The apparatus of claim 9, wherein, while the track is mounted along one of the first and second board edges, the second shield edge is magnetically securable to the other of the first and second board edges so as to limit unintended sliding of the at least one shield member along the track.

11. The apparatus of claim 10, wherein the at least one shield member comprises a first shield member and a second shield member, the first and second shield members being independently slidable along the track between an adjoined arrangement and a spaced apart arrangement in which a longitudinal gap is defined between the first and second shield members.

12. The apparatus of claim 1, wherein the at least one radiation shield comprises an adjustable screen assembly for shielding radiation scatter above the procedure table, and the adjustable screen assembly comprises:
   a bracket comprising a mount and a ledge extending away from the mount, the mount being mountable to the board along one of the first and second board edges;
   a clamping mechanism attached to the ledge;
   a shaft extending from a first shaft end to a second shaft end along a shaft axis; and
   a screen connected to the shaft proximate to the second shaft end,
   wherein the clamping mechanism is configured to clamp the shaft to maintain a position of the screen above the board.

13. The apparatus of claim 12, wherein the clamping mechanism comprises a rotary joint, the rotary joint comprising a shaft opening configured to receive the shaft, the rotary joint being rotatable relative to the ledge about a rotation axis orthogonal to the shaft axis, and the rotary joint is rotatable about the rotation axis to vary an angle between the shaft and the bracket to adjust the position of the screen above the board.

14. The apparatus of claim 13, wherein the ledge comprises a plurality of holes arranged circumferentially around the rotary joint, the clamping mechanism comprises a tack engageable with any one of the holes of the ledge to maintain an angle between the shaft and the mount, and the angle maintained between the shaft and the mount is determined by which one of the holes in the ledge is engaged by the tack.

15. The apparatus of claim 14, wherein the shaft is translatable through the shaft opening to vary a distance between the screen and the bracket to adjust the position of the screen above the board.

16. The apparatus of claim 15, wherein the shaft is rotatable about the shaft axis to vary an angle between the screen and the bracket to adjust the position of the screen above the board, and the rotary joint comprises a compression screw engageable with the shaft to restrict translation and rotation of the shaft in the shaft opening.

17. The apparatus of claim 12, wherein the screen comprises:
   a frame member extending away from the shaft axis; and
   a plurality of strips suspended from the frame member, each strip extending from a first strip edge to a second strip edge, the first strip edge of each strip being connected to the frame member.

18. The apparatus of claim 1, wherein the at least one radiation shield comprises a skirt for shielding radiation scatter below the procedure table, the at least one peg of the skirt comprises spaced apart first and second pegs, the first and second pegs being correspondingly engageable with a pair of the apertures in the board.

19. An apparatus for shielding radiation emitted during a medical procedure, the apparatus comprising:
   a board positionable on top of a procedure table, the board extending laterally between a first board edge and a second board edge; and
   a body shield assembly for shielding a patient supported above the procedure table from radiation, the body shield assembly comprising:
   a longitudinally extending track removably mountable to the board along one of the first and second board edges; and
   at least one shield member extending from a first shield edge to a second shield edge, the first shield edge being attached to and slidable along the track.

20. An apparatus for shielding radiation emitted during a medical procedure, the apparatus comprising:
   a board positionable on top of a procedure table, the board extending laterally between a first board edge and a second board edge, and longitudinally between a third board edge and a fourth board edge; and
   an adjustable screen assembly for shielding radiation scatter above the procedure table, the adjustable screen assembly comprising:
   a bracket comprising a mount and a ledge extending away from the mount, the mount being removably mountable to the board along one of the board edges;
   a clamping mechanism attached to the ledge;
   a shaft extending from a first shaft end to a second shaft end along a shaft axis; and
   a screen connected to the shaft proximate to the second shaft end, wherein the clamping mechanism is configured to clamp the shaft to maintain a position of the screen above the board.

\* \* \* \* \*